(12) United States Patent
Sato et al.

(10) Patent No.: US 12,226,262 B2
(45) Date of Patent: Feb. 18, 2025

(54) PROCESSING APPARATUS FOR TRANSFORMING ULTRASOUND DATA ACQUIRED THROUGH A FIRST NUMBER OF TRANSMISSIONS INTO DATA ACQUIRED THROUGH A HIGHER NUMBER OF TRANSMISSIONS

(71) Applicant: Canon Medical Systems Corporation, Otawara (JP)

(72) Inventors: Takeshi Sato, Nasushiobara (JP); Ryota Osumi, Nasushiobara (JP); Takatoshi Okumura, Yaita (JP); Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 236 days.

(21) Appl. No.: 16/744,246

(22) Filed: Jan. 16, 2020

(65) Prior Publication Data

US 2020/0281570 A1   Sep. 10, 2020

(30) Foreign Application Priority Data

Jan. 17, 2019 (JP) .................. 2019-006362
Jan. 17, 2019 (JP) .................. 2019-006363
Jan. 17, 2019 (JP) .................. 2019-006364

(51) Int. Cl.
    *A61B 8/08* (2006.01)
    *A61B 8/00* (2006.01)
    (Continued)

(52) U.S. Cl.
    CPC ............. *A61B 8/5207* (2013.01); *A61B 8/54* (2013.01); *A61B 8/56* (2013.01); *B06B 1/0215* (2013.01); *G06N 3/08* (2013.01); *B06B 2201/76* (2013.01)

(58) Field of Classification Search
    CPC ...... B06B 1/0215; G06N 3/08; G06N 3/0454; G06N 3/084; A61B 5/7264; A61B 8/481;
    (Continued)

(56) References Cited

U.S. PATENT DOCUMENTS

2015/0320398 A1   11/2015   Honjo et al.
2016/0183917 A1    6/2016   Kameishi et al.
(Continued)

FOREIGN PATENT DOCUMENTS

JP   H11-031214 A    2/1999
JP   2012-200460 A   10/2012
(Continued)

OTHER PUBLICATIONS

Gasse, M, et al., "High-Quality Plane Wave Compounding Using Convolutional Neural Networks", IEEE Transactions on Ultrasonics, Ferroelectrics, and Frequency Control, vol. 64, No. 10, Oct. 2017, pp. 1637-1639.

(Continued)

*Primary Examiner* — Joel Lamprecht
*Assistant Examiner* — Nyrobi Celestine
(74) *Attorney, Agent, or Firm* — Oblon, McClelland, Maier & Neustadt, L.L.P.

(57) ABSTRACT

According to one embodiment, an apparatus includes processing circuitry. The processing circuitry acquires output data from a trained model by entering examination data acquired at an examination, the examination data corresponding to first data, the output data corresponding to second data, into the trained model configured to, based on the first data acquired through transmission of an ultrasound wave for a first number of times, output the second data acquired through transmission of an ultrasound wave for a second number of times that is greater than the first number of times.

7 Claims, 29 Drawing Sheets

(51) Int. Cl.
B06B 1/02 (2006.01)
G06N 3/08 (2023.01)

(58) Field of Classification Search
CPC ......... A61B 8/56; A61B 8/54; G01S 7/52038; G01S 7/52039
See application file for complete search history.

(56) References Cited

U.S. PATENT DOCUMENTS

| | | | |
|---|---|---|---|
| 2018/0177461 A1* | 6/2018 | Bell | A61B 5/0095 |
| 2018/0330518 A1* | 11/2018 | Choi | A61B 8/085 |
| 2019/0130564 A1* | 5/2019 | Kawabata | A61B 8/5246 |
| 2019/0295295 A1* | 9/2019 | Hyun | A61B 8/5207 |
| 2019/0336108 A1* | 11/2019 | Hope Simpson | A61B 8/0891 |
| 2019/0362522 A1* | 11/2019 | Han | A61N 5/1039 |
| 2020/0060652 A1* | 2/2020 | Dahl | G06N 3/08 |
| 2021/0265042 A1* | 8/2021 | Kim | A61B 8/58 |

FOREIGN PATENT DOCUMENTS

| | | |
|---|---|---|
| JP | 5534649 B2 | 7/2014 |
| JP | 2015-226762 A | 12/2015 |
| JP | 6425994 B2 | 11/2018 |
| WO | WO 2014/069558 A1 | 5/2014 |
| WO | WO 2018/127497 A1 | 7/2018 |

OTHER PUBLICATIONS

Japanese Office Action dated Jan. 10, 2023, issued in Japanese Patent Application No. 2019-006362.

Japanese Office Action dated Mar. 12, 2024, issued in Japanese Patent Application No. 2023-102409.

* cited by examiner

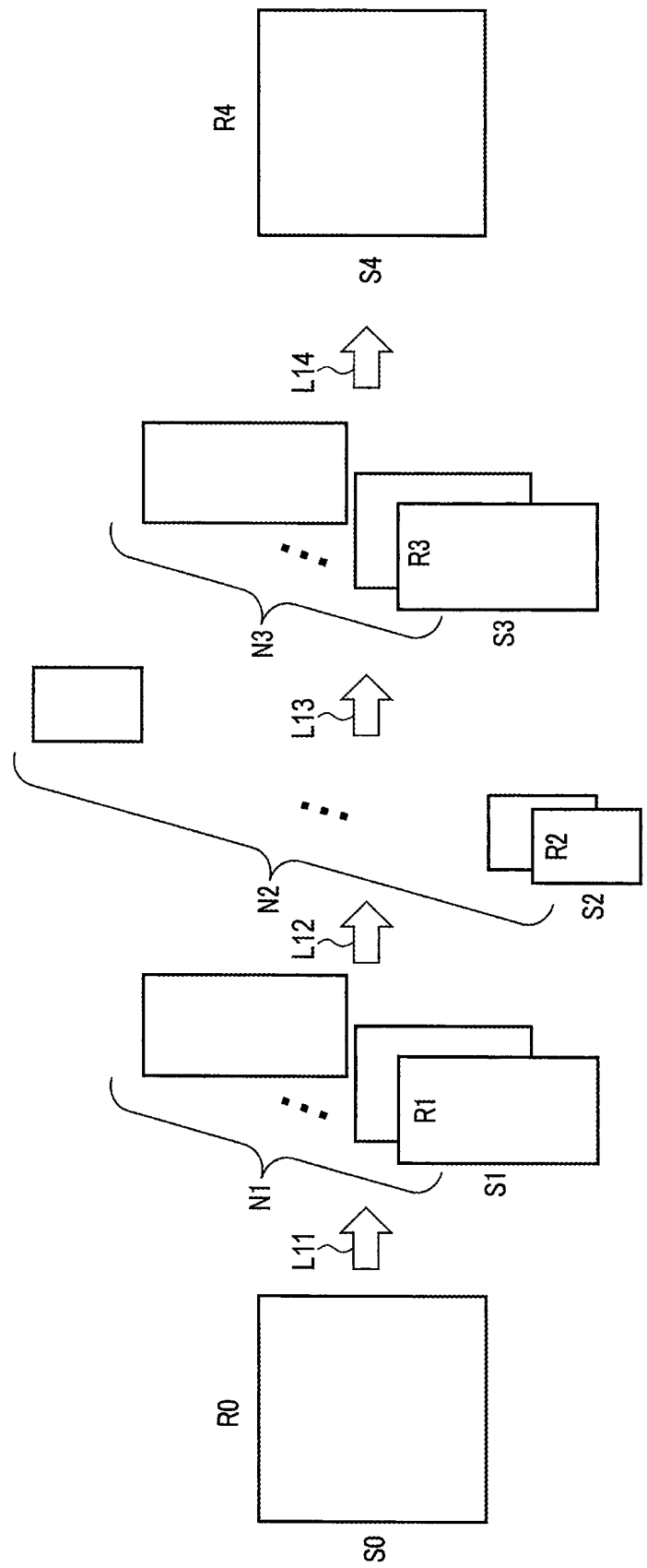
F I G. 5

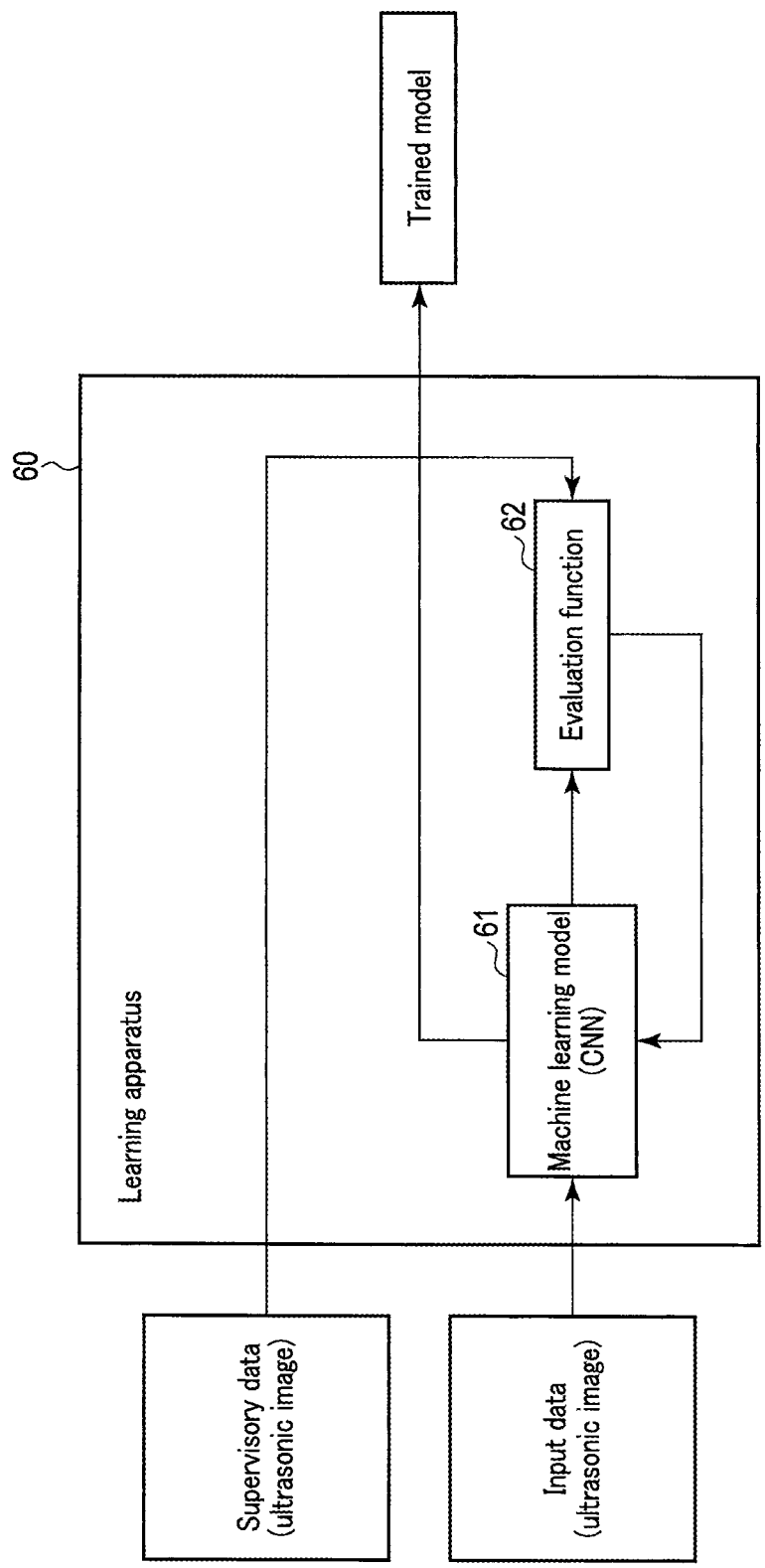
F I G. 11

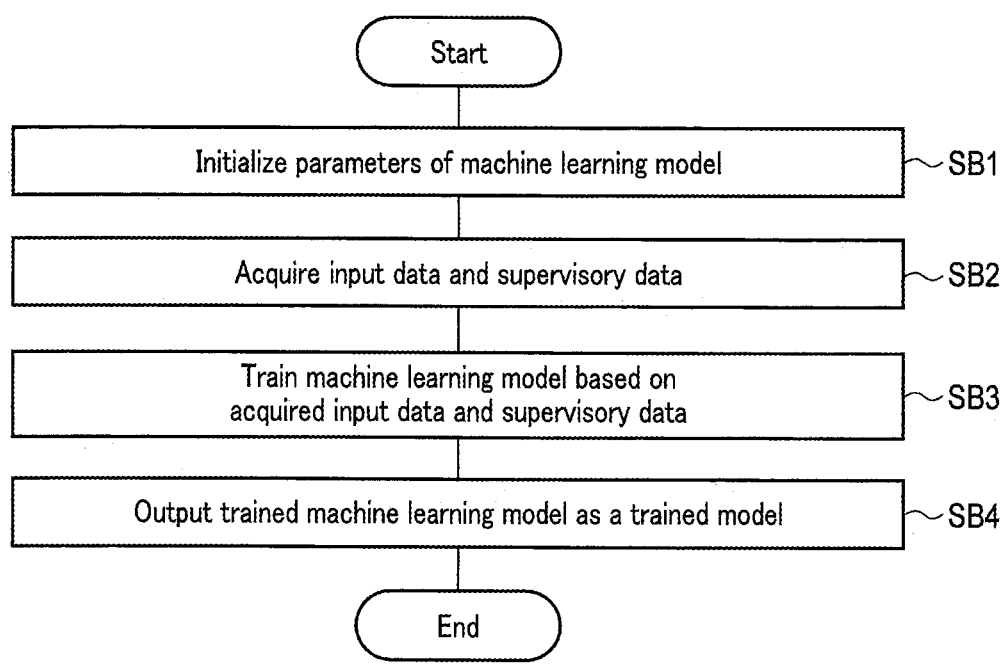
F I G. 12

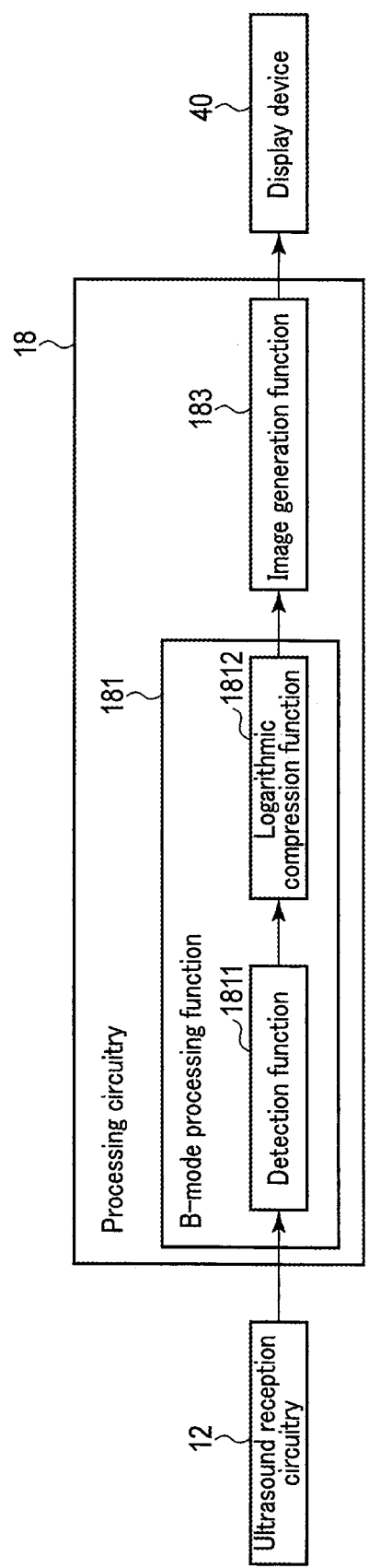
F I G. 13

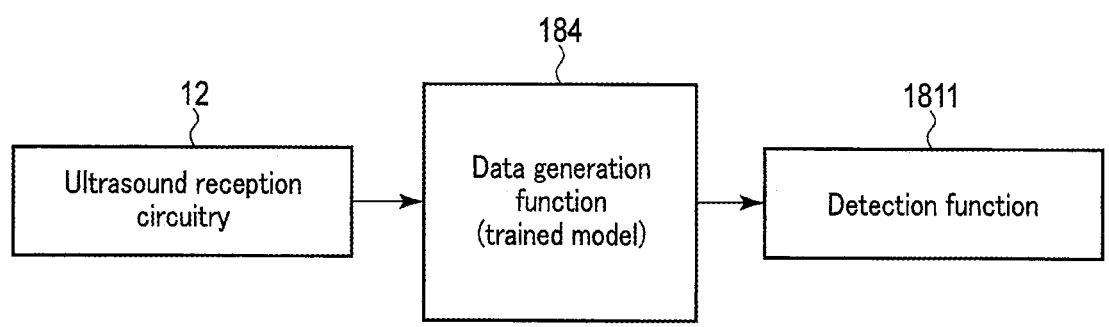
F I G. 14

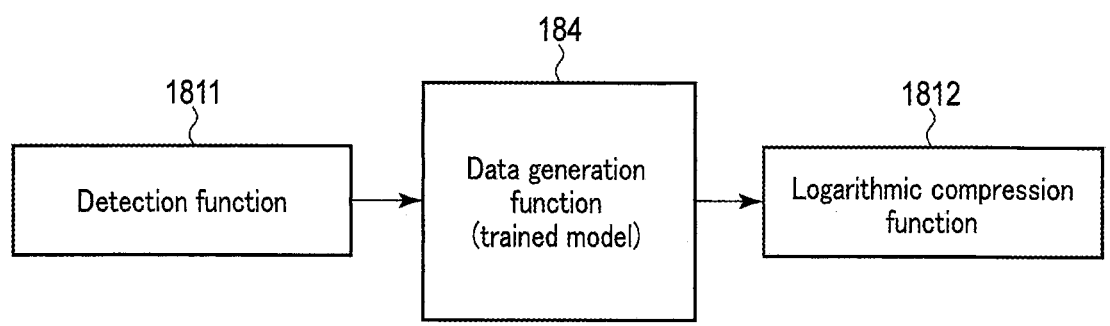
F I G. 16
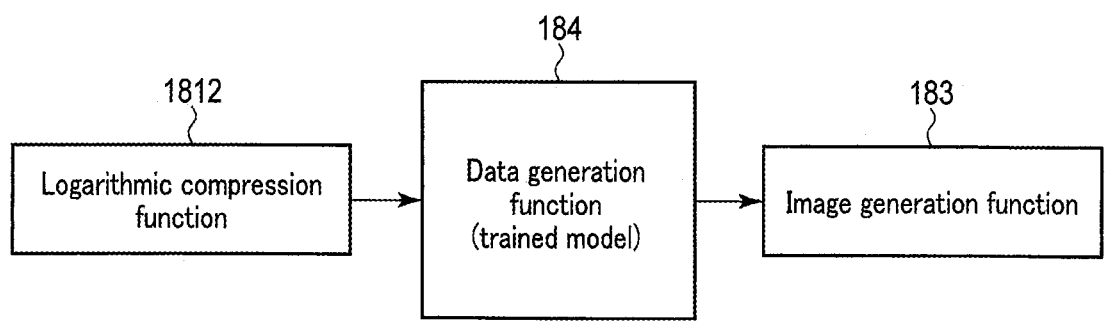
F I G. 17

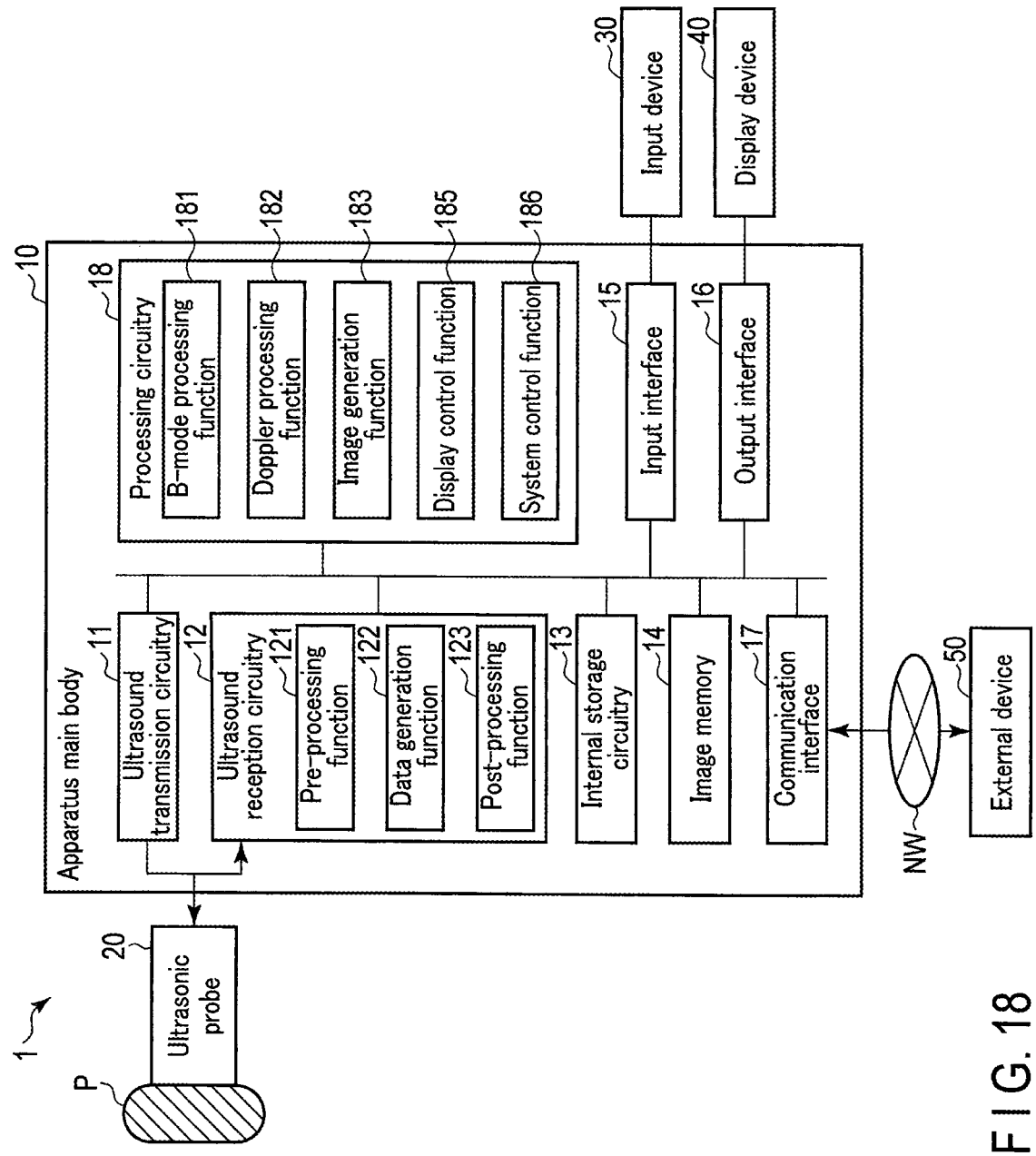
F I G. 18

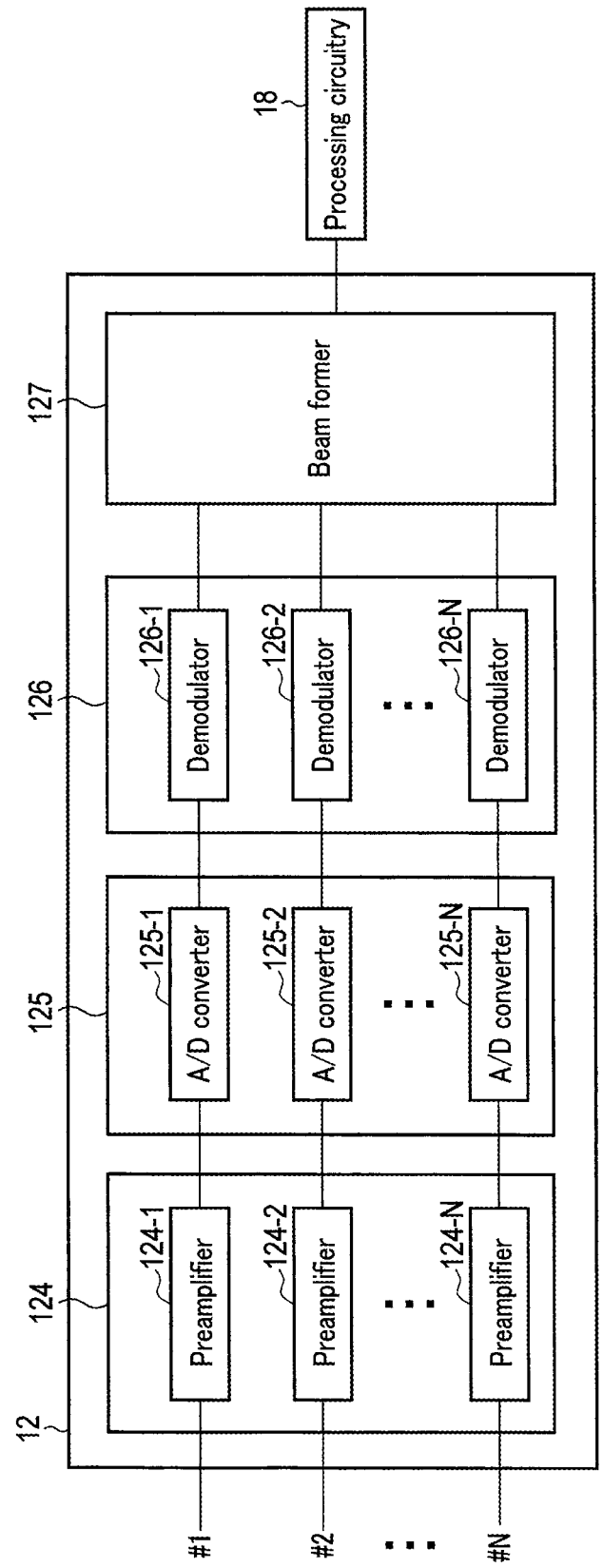
F I G. 20

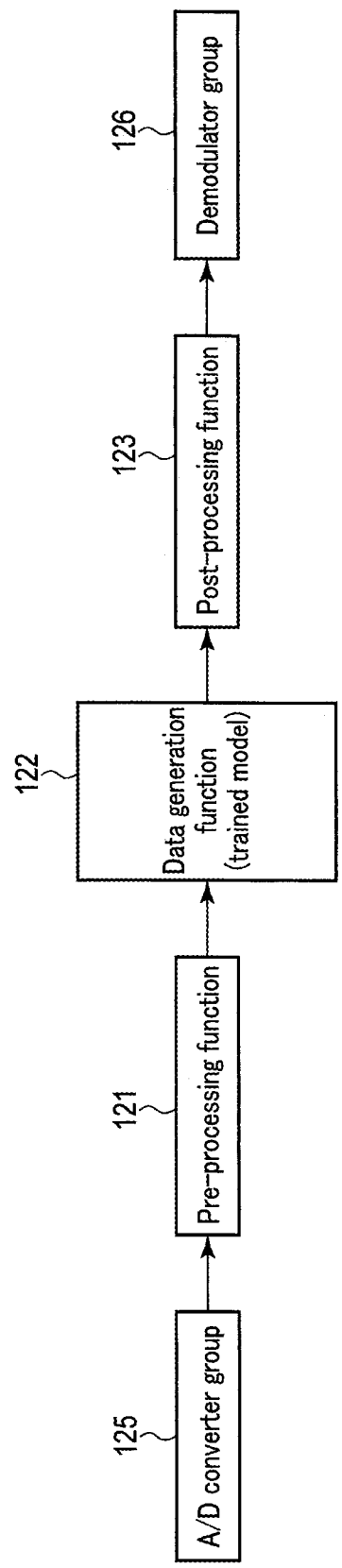
F I G. 22

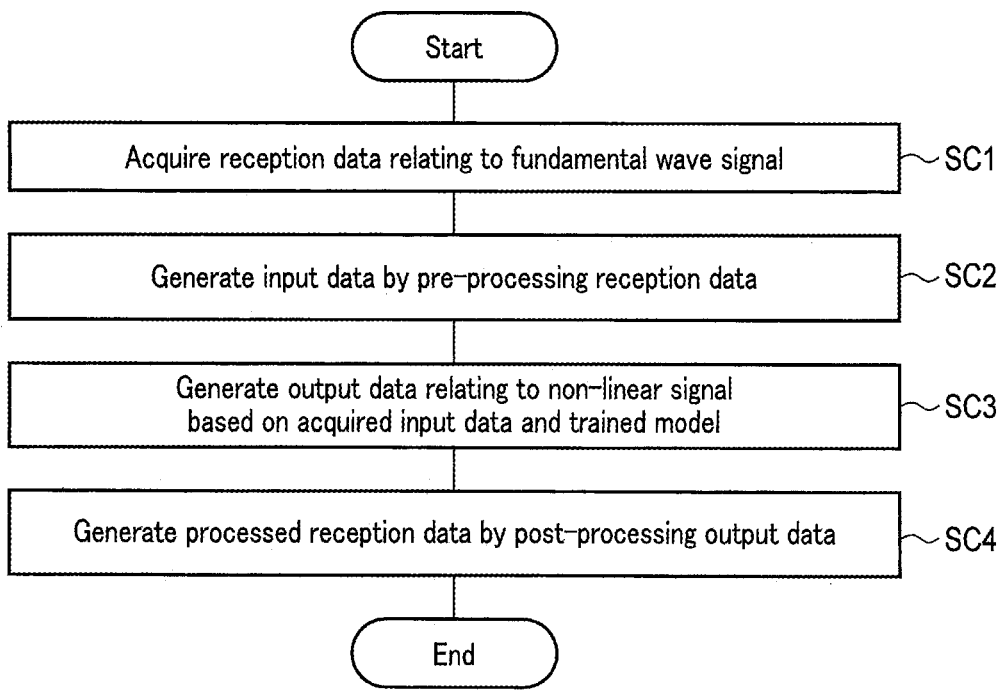
F I G. 24
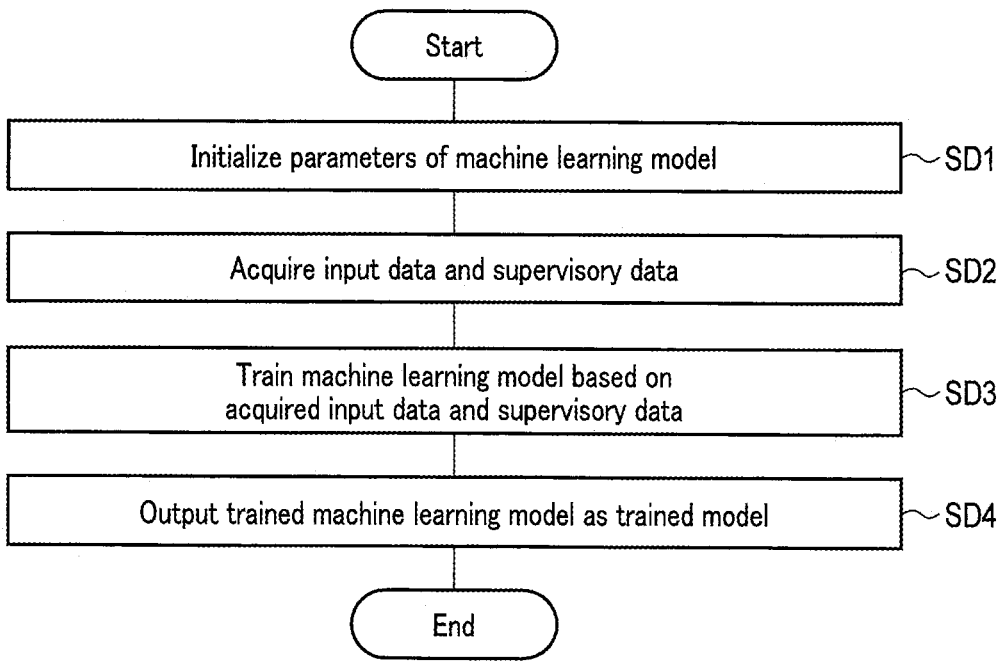
F I G. 25

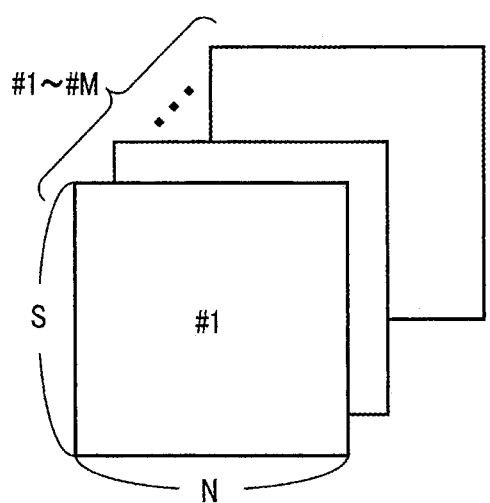
F I G. 26

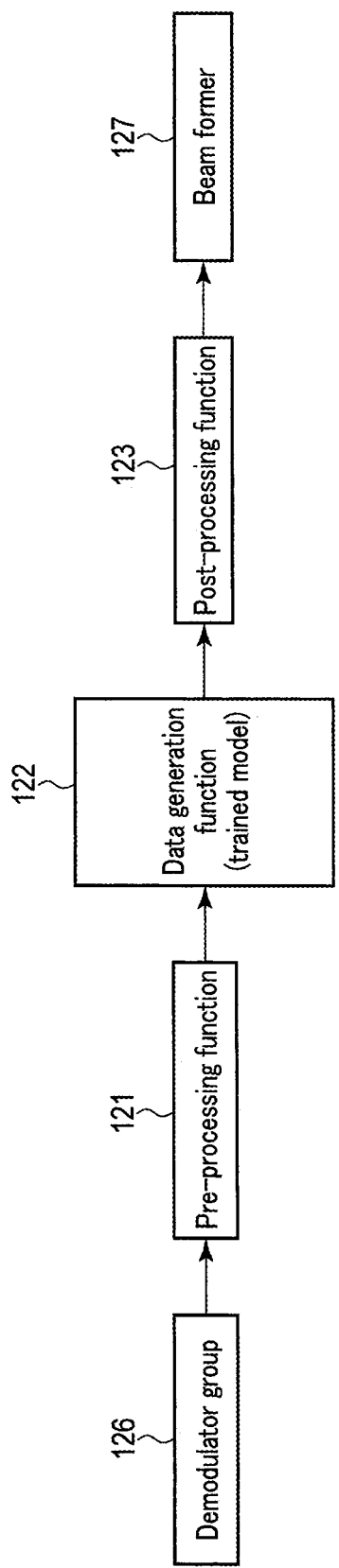
F I G. 27

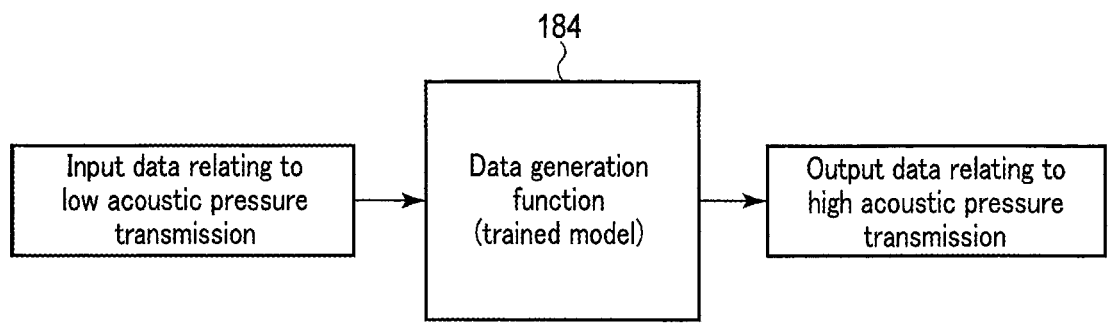
F I G. 36
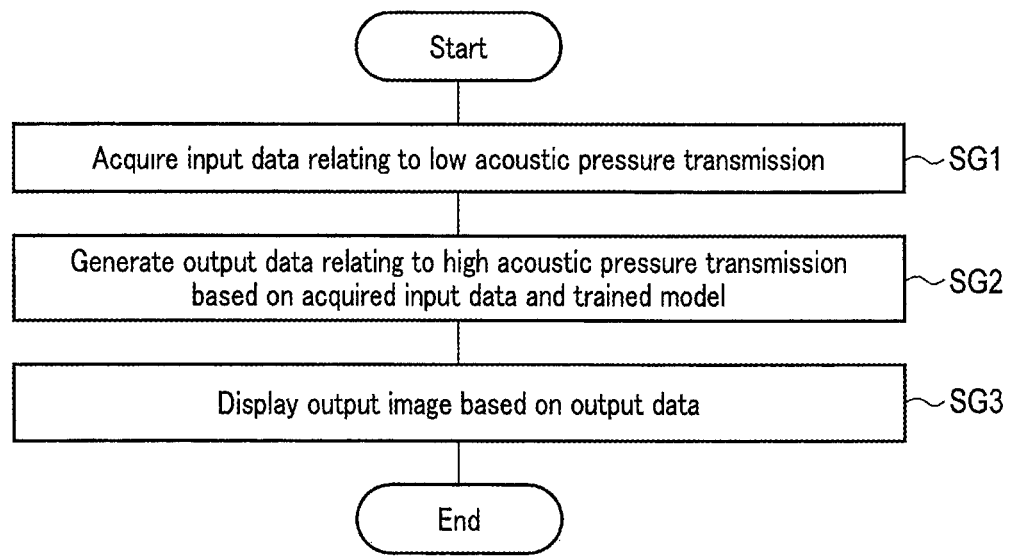
F I G. 37

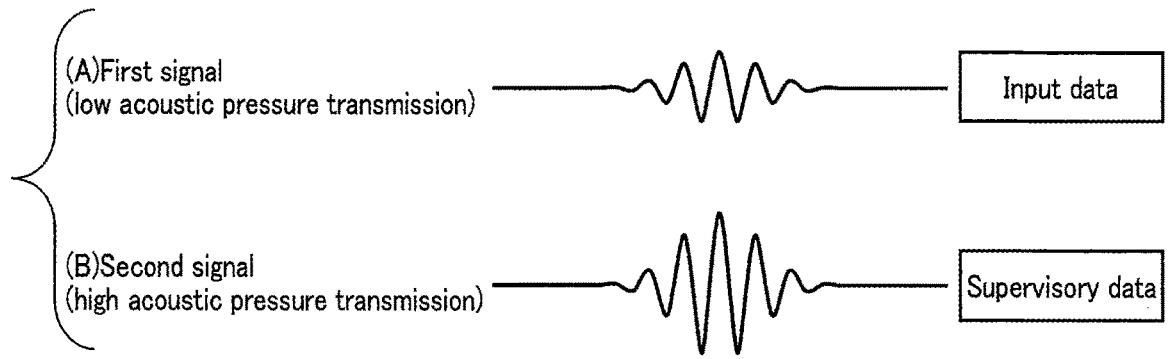
F I G. 38
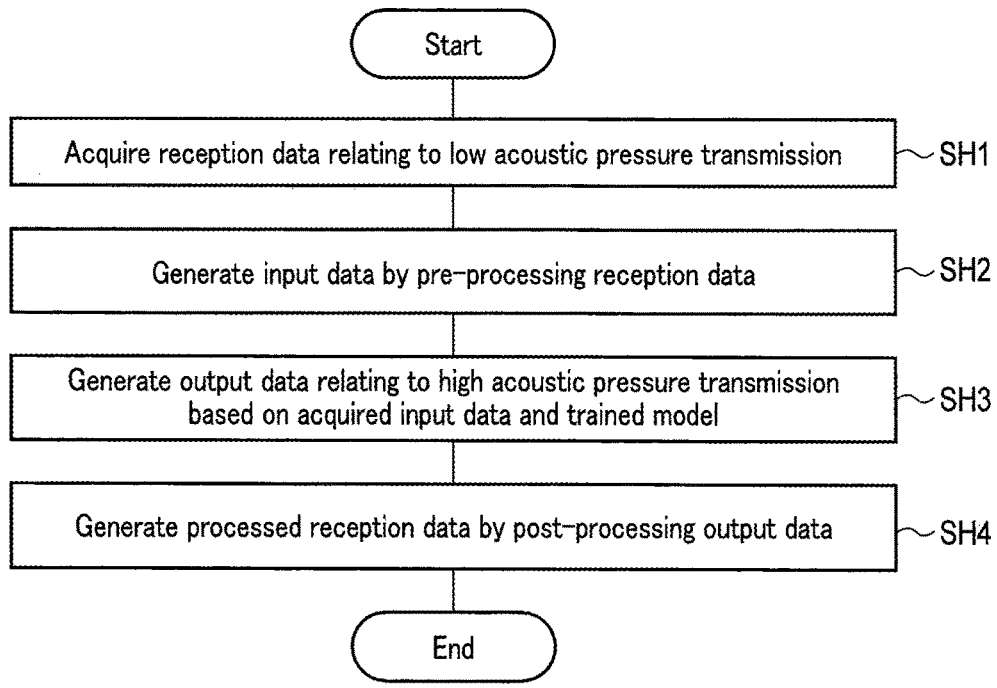
F I G. 39

PROCESSING APPARATUS FOR TRANSFORMING ULTRASOUND DATA ACQUIRED THROUGH A FIRST NUMBER OF TRANSMISSIONS INTO DATA ACQUIRED THROUGH A HIGHER NUMBER OF TRANSMISSIONS

CROSS-REFERENCE TO RELATED APPLICATIONS

This application is based upon and claims the benefit of priority from Japanese Patent Applications No. 2019-006362, filed Jan. 17, 2019; and No. 2019-006363, filed Jan. 17, 2019; and No. 2019-006364, filed Jan. 17, 2019; the entire contents of all of which are incorporated herein by reference.

FIELD

Embodiments described herein relate generally to an ultrasonic diagnostic apparatus.

BACKGROUND

In relation to an ultrasonic diagnostic apparatus, in response to transmission of an ultrasonic frequency, a harmonic component of the ultrasonic frequency returns from a living body, and through the use of this property, imaging for forming an ultrasonic image based on harmonic components, which is referred to as tissue harmonic imaging (THI), is generally known. With the THI, a high-quality ultrasonic image which has fewer sidelobe artifacts than an ultrasonic image based on a fundamental component can be obtained.

The known methods of THI include filtering, pulse inversion (broadly speaking, one type of phase modulation), and amplitude modulation. With filtering, the process can be completed in one transmission/reception. However, the resultant bandwidth, which is too narrow, lowers the axial resolution, and therefore is not commonly used. The pulse inversion (or phase modulation) allows for a broadband reception and thus improves resolution. This technique, however, requires two or more transmissions/receptions, and thus produces a disadvantage with regard to the frame rate. The amplitude modulation also requires two or more transmissions/receptions, which results in a disadvantage with regard to the frame rate.

An ultrasonic diagnostic apparatus is designed to sum up multiple ultrasonic signals acquired through multiple ultrasonic transmissions with respect to one scan direction to acquire an add signal. For this add signal, it is known that a signal-to-noise ratio greater than an ultrasonic signal from a single ultrasonic transmission can be attained. However, since multiple ultrasonic transmissions need to be conducted, the add signal is disadvantageous with regard to the number of transmissions and the frame rate.

BRIEF DESCRIPTION OF THE DRAWINGS

FIG. 5 is a diagram explaining the data generation function of the processing circuitry.
FIG. 11 is a diagram showing a specific example of the generation of a trained model by the learning apparatus.
FIG. 12 is a flowchart of an exemplary operation of the learning apparatus generating a trained model.
FIG. 13 is a diagram explaining the data flow from ultrasound reception circuitry to the processing circuitry and to the display device.
FIG. 14 is a diagram showing an example of part of the implementation of the data generation function.
FIG. 16 is a diagram showing an example of part of the implementation of the data generation function.
FIG. 17 is a diagram showing an example of part of the implementation of the data generation function.
FIG. 18 is a block diagram showing an exemplary structure of an ultrasonic diagnostic apparatus according to the second embodiment.
FIG. 20 is a block diagram showing an exemplary structure of the ultrasound reception circuitry and processing circuitry.
FIG. 22 is a diagram showing an example of part of the implementation of the data generation function.
FIG. 24 is a flowchart of an exemplary operation of the ultrasound reception circuitry with the data generation function.
FIG. 25 is a flowchart of an exemplary operation of the learning apparatus generating a trained model.
FIG. 26 is a diagram showing exemplary input data that is input to the data generation function.
FIG. 27 is a diagram explaining an exemplary data flow in the ultrasound reception circuit.

FIG. 36 is a diagram explaining a concept of data input to and output from the data generation function of processing circuitry according to the sixth embodiment.

FIG. 37 is a flowchart of an exemplary operation of the processing circuitry with the data generation function according to the sixth embodiment.

FIG. 38 is a diagram showing exemplary transmission waveforms of ultrasound waves for the generation and use of a trained model according to the sixth embodiment.

FIG. 39 is a flowchart of an exemplary operation of the ultrasound reception circuitry with the data generation function according to the sixth embodiment.

DETAILED DESCRIPTION

In general, an apparatus according to one embodiment includes processing circuitry. The processing circuitry acquires output data from a trained model by entering examination data acquired at an examination, the examination data corresponding to first data and the output data corresponding to second data, into the trained model configured to, based on the first data acquired through transmission of an ultrasound wave for a first number of times, output the second data acquired through transmission of an ultrasound wave for a second number of times that is greater than the first number of times.

The embodiments will be explained below with reference to the drawings. The ultrasonic diagnostic apparatus according to this embodiment applies a data generation function, which is a trained model, to input data, which is a reception signal acquired in response to the transmission of a fundamental wave signal of a ultrasonic wave, thereby generating output data based on a non-linear signal such as a harmonic signal of an ultrasonic wave.

First Embodiment

Figure 1:
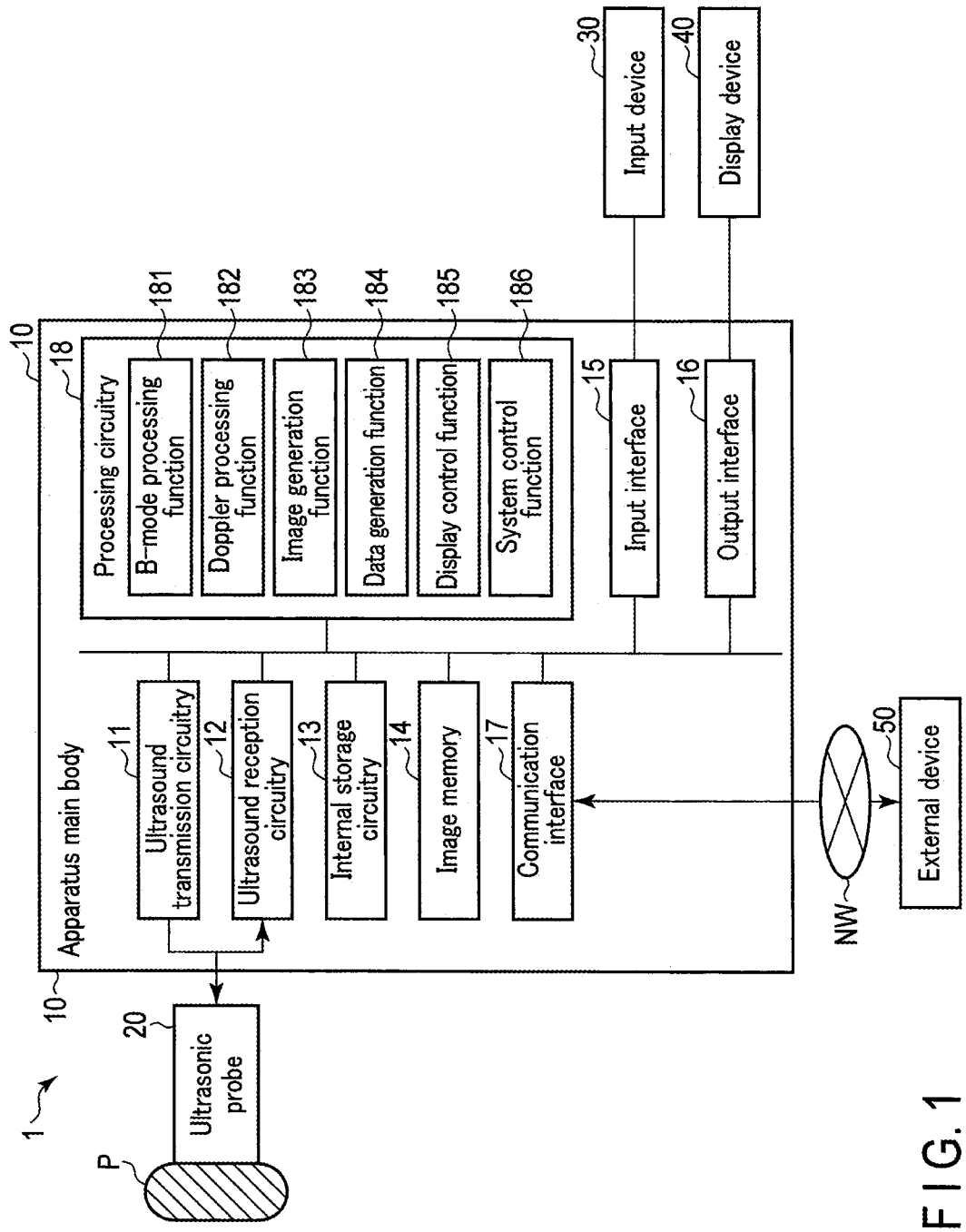
FIG. 1 is a block diagram illustrating an exemplary configuration of an ultrasonic diagnostic apparatus according to the first embodiment.

FIG. 1 is a block diagram illustrating an exemplary configuration of an ultrasonic diagnostic apparatus 1 according to the first embodiment. The ultrasonic diagnostic apparatus 1 includes an apparatus main body 10 and an ultrasonic probe 20. The apparatus main body 10 is connected to an input device 30 and display device 40. The apparatus main body 10 is also connected to an external device 50 by way of a network NW.

The ultrasonic probe 20 may implement ultrasound scanning onto a scan area of a living body P, which is a subject, under the control of the apparatus main body 10. The ultrasonic probe 20 may include a plurality of piezoelectric vibrators, matching layers provided on the respective piezoelectric vibrators, and a backing material that prevents the ultrasonic waves from propagating in a direction rearward from the piezoelectric vibrators. The ultrasonic probe 20 may be a one-dimensional array linear probe in which a plurality of ultrasonic vibrators are arranged in a predetermined direction. The ultrasonic probe 20 is detachably coupled to the apparatus main body 10. The ultrasonic probe 20 may be provided with a button pressed when performing offset processing or freezing of an ultrasonic image.

The piezoelectric vibrators generate ultrasonic waves based on a drive signal supplied from the ultrasound transmission circuitry 11 of the apparatus main body 10, which will be described later. The ultrasonic waves are thereby transmitted from the ultrasonic probe 20 to the living body P. When an ultrasonic wave is transmitted from the ultrasonic probe 20 to the living body P, the transmitted ultrasonic wave is sequentially reflected on the acoustic impedance discontinuous surface of the internal tissue of the living body P, and is received as reflection wave signals by multiple piezoelectric vibrators. The amplitude of a received reflection wave signal depends on the difference in acoustic impedance on the discontinuous surface from which the ultrasonic wave is reflected. If the transmitted ultrasound pulse is reflected, for example, from a moving bloodstream or the surface of a cardiac wall or the like, the frequency of the resultant reflection wave signal is shifted by the Doppler effect, with the shift depending on a velocity component of a moving object in the ultrasound transmission direction. The ultrasonic probe 20 receives a reflection signal from the living body P and converts it into an electric signal.

FIG. 1 illustrates only a connection between the ultrasonic probe 20 used for ultrasound scanning and the apparatus main body 10. The apparatus main body 10, however, can be coupled to a plurality of ultrasonic probes. Which of the coupled ultrasonic probes is to be used for ultrasound scanning can be freely selected through a switch operation.

The apparatus main body 10 generates an ultrasonic image based on a reflection wave signal received by the ultrasonic probe 20. The apparatus main body 10 includes ultrasound transmission circuitry 11, ultrasound reception circuitry 12, internal storage circuitry 13, an image memory 14, an input interface 15, an output interface 16, a communication interface 17, and processing circuitry 18.

The ultrasound transmission circuitry 11 is a processor that supplies a drive signal to the ultrasonic probe 20. The ultrasound transmission circuitry 11 is realized, for example, by a trigger generation circuit, a delay circuit, and a pulser circuit. A trigger generating circuit repeatedly generates a rate pulse for forming a transmission ultrasonic wave at a predetermined rate frequency. The delay circuit supplies a delay time for each piezoelectric vibrator to each rate pulse generated by the trigger generation circuit, where this delay time is required to converge the ultrasonic wave generated by the ultrasonic probe into a beam and to determine the transmission directivity. The pulser circuit applies a drive signal (drive pulse) to the multiple ultrasonic vibrators arranged in the ultrasonic probe 20 at the timing based on a rate pulse. The delay circuit varies the delay times that are to be supplied to the rate pulses so that the transmission direction from the surface of the piezoelectric vibrators can be freely adjusted.

The ultrasound reception circuitry 12 is a processor that performs various kinds of processing on the reflection wave signal received by the ultrasonic probe 20 to generate a reception signal. The ultrasound reception circuitry 12 may be realized by a preamplifier, A/D converter, demodulator, and beam former. The preamplifier performs gain correction processing by amplifying the reflection wave signal received by the ultrasonic probe 20 for each channel. The A/D converter converts the gain-corrected reflection wave signal into a digital signal. The demodulator demodulates the digital signal. The beam former may supply, to the demodulated digital signal, a delay time required to determine the reception directivity, and adds the digital signals to which the delay time is supplied. Through the addition processing by the beam former, a reception signal is generated in which a reflection component from the direction corresponding to the reception directivity is emphasized.

The internal storage circuitry 13 includes, for example, a magnetic or optical storage medium, or a storage medium such as a semiconductor memory that can be read by a processor. The internal storage circuitry 13 stores therein programs, various types of data, and the like for realizing ultrasound transmission/reception. The programs and data may be pre-stored in the internal storage circuitry 13. Alternatively, they may be stored and distributed in a non-transitory storage medium, read from the non-transitory storage medium, and installed in the internal storage circuitry 13.

The internal storage circuitry 13 further stores a trained model, which will be described later. The internal storage circuitry 13 may store the trained model at the time of shipping the ultrasonic diagnostic apparatus 1. Alternatively, the internal storage circuitry 13 may store a trained model acquired, for example, from an external device 50 after the shipping of the ultrasonic diagnostic apparatus 1.

Furthermore, the internal storage circuitry 13 stores B-mode image data generated by the processing circuitry 18 and the like in accordance with an operation that is input via the input interface 15. The internal storage circuitry 13 may transfer the stored data to an external device 50 via the communication interface 17.

The internal storage circuitry 13 may be a driving device that reads and writes various types of information with respect to a portable storage medium such as a CD-ROM drive, DVD drive, or flash memory. The internal storage circuitry 13 may write the stored data into a portable storage medium or enter the data into an external device 50 via a portable storage medium.

The image memory 14 may include a magnetic storage medium, an optical storage medium, or a storage medium such as a semiconductor memory that can be read by a processor. The image memory 14 stores therein image data corresponding to a plurality of frames, which is input via the input interface 15 immediately before a freeze operation. The image data stored in the image memory 14 may be sequentially displayed (as moving images).

The internal storage circuitry 13 and the image memory 14 may not necessarily be realized by independent storage devices. The internal storage circuitry 13 and image memory 14 may be realized by a single storage device. In addition, the internal storage circuitry 13 and image memory 14 may each be realized by multiple storage devices.

The input interface 15 receives various commands from the operator through the input device 30. The input device 30 may include a mouse, a keyboard, panel switches, slider switches, a track ball, a rotary encoder, an operation panel, a touch command screen (TCS), and the like. The input interface 15 may be connected to the processing circuitry 18 via a bus so as to convert an operation command that is input by the operator to an electric signal, and to output the electric signal to the processing circuitry 18. The input interface 15 is not limited to a component connected to a physical operation component such as a mouse and keyboard. Examples of the input interface include a circuit configured to receive an electric signal corresponding to an operation command that is input from an external input device provided separately from the ultrasonic diagnostic apparatus 1 and to output this electric signal to the processing circuitry 18.

The output interface 16 may be an interface to output an electric signal from the processing circuitry 18 to the display device 40. The display device 40 includes a liquid crystal display, an organic EL display, an LED display, a plasma display, a CRT display, or can be any other display. The output interface 16 may be connected to the processing circuitry 18 via a bus, and output an electric signal from the processing circuitry 18 to a display device.

The communication interface 17 may be connected to an external device 50 via a network NW so as to perform data communications with the external device 50.

The processing circuitry 18 may be a processor that serves as the center of the ultrasonic diagnostic apparatus 1. The processing circuitry 18 implements the program stored in the internal storage circuitry 13, thereby realizing the functions corresponding to the program. The processing circuitry 18 may have a B-mode processing function 181, a Doppler processing function 182, an image generation function 183, a data generation function 184, a display control function 185, and a system control function 186.

The B-mode processing function 181 is configured to generate B-mode data based on a reception signal received from the ultrasound reception circuitry 12. With the B-mode processing function 181, the processing circuitry 18 implements envelope detection processing, logarithmic compression processing and the like on the reception signal received from the ultrasound reception circuitry 12, and thereby generates data (B-mode data) that expresses the signal intensity with luminance. The generated B-mode data is stored in a raw data memory (not shown) as B-mode raw data on two-dimensional ultrasound scanning lines (rasters).

The Doppler processing function 182 is configured to generate data (Doppler information) by extracting motion information of a moving object in the Region Of Interest (ROI) defined in the scan area based on the Doppler effect, through the frequency analysis on the reception signal received from the ultrasound reception circuitry 12. The generated Doppler information is stored in the raw data memory (not shown) as Doppler raw data on two-dimensional ultrasound scanning lines.

The image generation function 183 is configured to generate B-mode image data based on the data generated with the B-mode processing function 181. For example, with the image generation function 183, the processing circuitry 18 converts (scan-converts) a scan line signal sequence of ultrasound scanning into a scan line signal sequence in a video format representatively used by television and thereby generates image data for display. In particular, the processing circuitry 18 implements a raw-pixel conversion such as coordinate conversion in accordance with the ultrasound scanning mode of the ultrasonic probe 20, on the B-mode raw data stored in the raw data memory, and thereby generates two-dimensional B-mode image data composed of pixels.

The data generation function 184 is configured to generate data for generating image data in conformance with the B-mode image data. With the data generation function 184, the processing circuitry 18 is configured to, by inputting input data based on a fundamental wave signal of an ultrasonic wave acquired from an examination, generate output data based on a non-linear signal. The data generation function 184 will be described in detail later.

The display control function 185 is configured to control the display of two-dimensional B-mode image data and image data on the display device 40. With the display control function 185, the processing circuitry 18 may superimpose on the two-dimensional B-mode image data an indication showing the ROI for collecting Doppler data. In accordance with a command that is input from the input device 30 by an operator, the processing circuitry 18 superimposes two-dimensional Doppler image data on the corresponding portion of the two-dimensional B-mode image data. Here, the processing circuitry may adjust the opacity of the two-dimensional Doppler image data to be superimposed, in accordance with the operator's command.

The processing circuitry 18 further implements, on the two-dimensional B-mode image data, various types of processing relating to the dynamic range, luminance (brightness), contrast, γ curve corrections and RGB conversion, so as to convert image data to video signals. The processing circuitry 18 displays the video signals on the display device 40. The processing circuitry 18 may generate a user interface (graphical user interface, or GUI) for an operator to input various commands on the input device, and displays the GUI on the display device 40.

The system control function 186 is configured to control the operations of the entire ultrasonic diagnostic apparatus 1 overall.

In general, the ultrasonic diagnostic apparatus 1 performs imaging using a harmonic component included in the reception signal, which is called harmonic imaging (HI), to generate B-mode image data. The ultrasonic diagnostic apparatus 1 may perform HI by adopting phase modulation (PM) or amplitude modulation (AM) in the ultrasound transmission. In HI, an image with reduced sidelobes can be obtained in contrast to image generation based on a fundamental component, and thus the image quality can be improved. The bearing resolution is improved as well in HI, in comparison with fundamental-component based image generation.

As HI, tissue harmonic imaging (THI) and contrast harmonic imaging (CHI) have been known. THI uses the property of an ultrasonic wave whose waveform becomes gradually distorted as it travels in living tissue, as a result of which a harmonic component comes to be included. In THI, the ultrasonic diagnostic apparatus 1 removes a fundamental component from a reception signal containing the fundamental component and a harmonic component, or extracts the harmonic component from the signal, thereby forming an image using this harmonic component. In CHI, the ultrasonic diagnostic apparatus 1 forms an image through an ultrasonic examination using an ultrasonic contrast agent, where harmonic components derived from this ultrasonic contrast agent are incorporated.

Exemplary phase modulation and amplitude modulation in HI of the ultrasonic diagnostic apparatus 1 will be described below.

Figure 2:
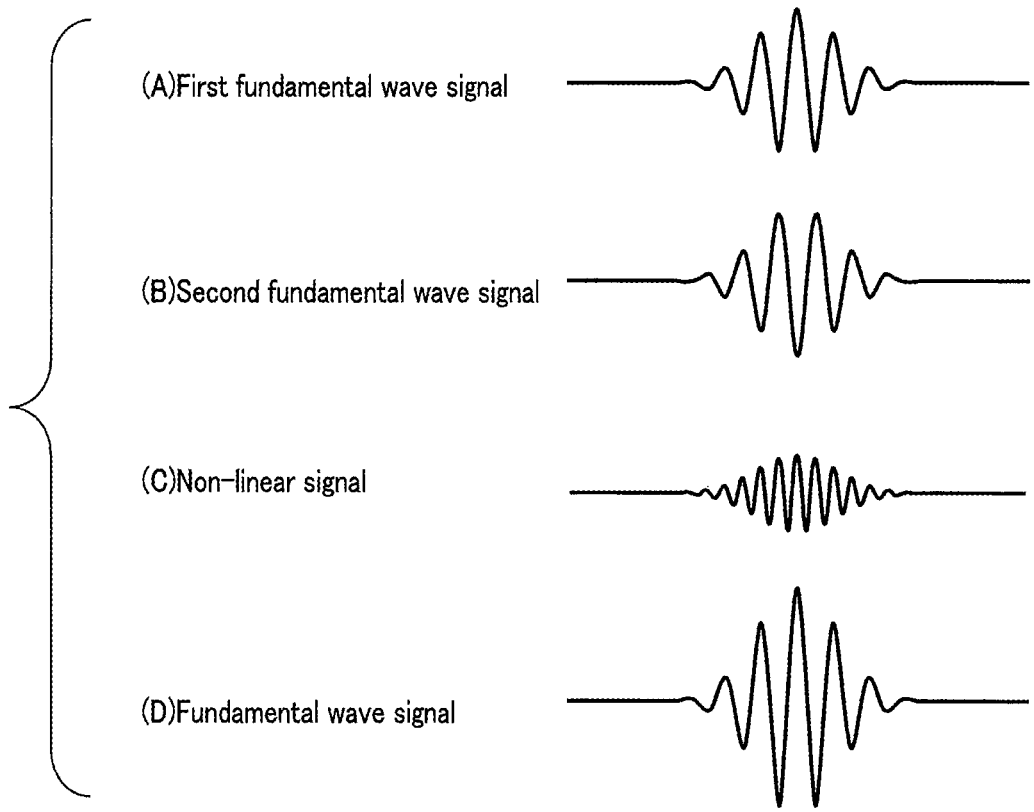
FIG. 2 is a diagram showing exemplary waveforms of ultrasonic waves in relation to phase modulation.

FIG. 2 is a diagram showing exemplary waveforms of ultrasonic waves in relation to the phase modulation. In the ultrasonic diagnostic apparatus 1, the ultrasound transmission circuitry 11 may conduct multiple ultrasound transmissions of different phases. For example, the ultrasound transmission circuitry 11 conducts two ultrasound transmissions on the same imaging area of the subject, using an ultrasonic wave as illustrated as (A) in FIG. 2, which is the first fundamental wave signal, and an ultrasonic wave as illustrated as (B) in FIG. 2, which is the second fundamental wave signal. The first fundamental wave signal and second fundamental wave signal are ultrasonic signals transmitted after beam forming by the ultrasound transmission circuitry 11. The first fundamental wave signal and second fundamental wave signal are ultrasonic waves composed of fundamental components. The second fundamental wave signal has an inverted phase to the phase of the first fundamental wave signal. The amplitude (acoustic pressure) of the first fundamental wave signal is the same as that of the second fundamental wave signal. The ultrasound reception circuitry 12 generates a first reception signal from the ultrasound transmission of the first fundamental wave signal and a second reception signal from the ultrasound transmission of the second fundamental wave signal.

With the B-mode processing function 181, the processing circuitry 18 may generate an add signal that is the sum of the first reception signal and the second reception signal, thereby acquiring a non-linear signal. FIG. 2 shows a non-linear signal as in (C), representing an add signal. The non-linear signal in (C) of FIG. 2 is a harmonic signal from which a fundamental component is removed, and which is composed of a harmonic component. By generating B-mode image data using this non-linear signal, or in other words through the THI, an image in which artifacts of sidelobes are mitigated can be obtained.

A non-linear signal denotes a signal that is not a fundamental wave signal (linear signal), such as a harmonic signal. For example, when an ultrasonic wave propagates through a living body that has a non-linear property, the waveform of the propagating ultrasonic wave is distorted, and a harmonic component that is not included in the transmission signal appears in the reception signal. This harmonic component (harmonic signal) will be referred to as a non-linear signal. The harmonic signal includes harmonic components included in a reception signal, such as high-order harmonic signals including a second harmonic signal, third harmonic signal, and fourth harmonic signal, as well as a decimal-order harmonic signal.

With the B-mode processing function 181, the processing circuitry 18 may generate a subtraction signal that represents a difference between the first reception signal based on the first fundamental wave signal and the second reception signal based on the second fundamental wave signal, thereby acquiring a fundamental wave signal. FIG. 2 shows a fundamental wave signal as in (D), which is a subtraction signal. The fundamental wave signal in (D) of FIG. 2 is composed of a fundamental component.

Figure 3:
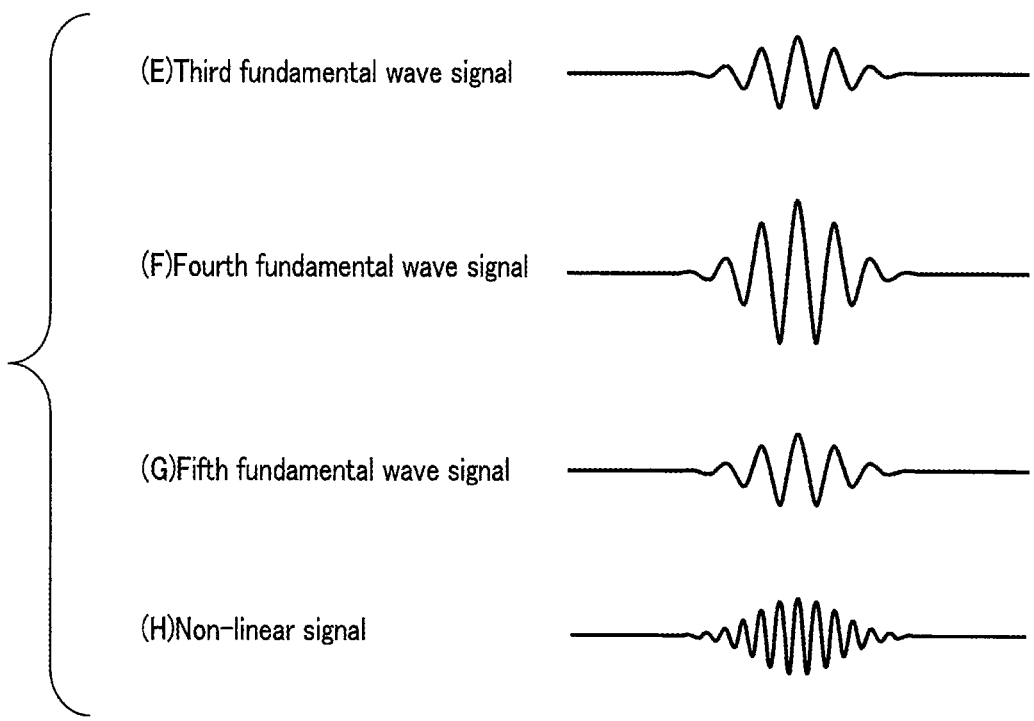
FIG. 3 is a diagram showing exemplary waveforms of ultrasonic waves in relation to amplitude modulation.

FIG. 3 is a diagram showing exemplary waveforms of ultrasonic waves in relation to amplitude modulation. In the ultrasonic diagnostic apparatus 1, the ultrasound transmission circuitry 11 may conduct multiple ultrasound transmissions of different acoustic pressures (amplitudes). For example, the ultrasound transmission circuitry 11 may conduct three ultrasound transmissions on the same imaging area of the subject, using an ultrasonic wave of a third fundamental wave signal as illustrated as (E) in FIG. 3, an ultrasonic wave of a fourth fundamental wave signal as illustrated as (F) in FIG. 3, and an ultrasonic wave of a fifth fundamental wave signal as (G) in FIG. 3. The third fundamental wave signal may be based on the ultrasound transmission from even-numbered channels (hereinafter referred to as even-numbered CH transmission) from among multiple channels (CH) of the ultrasonic probe 20 (unit of one-dimensional array of ultrasonic vibrators). The fourth fundamental wave signal may be based on the ultrasound transmission from all the channels of the ultrasonic probe 20 (hereinafter referred to as full CH transmission). The fifth fundamental wave signal may be based on the ultrasound transmission from the odd-numbered channels (hereinafter referred to as odd-numbered CH transmission). The third fundamental wave signal, fourth fundamental wave signal, and fifth fundamental wave signal are ultrasonic signals transmitted after beam forming by the ultrasonic transmission circuitry 11. The third fundamental wave signal, fourth fundamental wave signal, and fifth fundamental wave signal are ultrasonic waves composed of fundamental components of the same phase. The acoustic pressure of the third fundamental wave signal is approximately equal to the acoustic pressure of the fifth fundamental wave signal. The acoustic pressure of the fourth fundamental wave signal is approximately twice as large as the acoustic pressures of the third fundamental wave signal and the fifth fundamental wave signal. The ultrasound reception circuitry 12 generates a third reception signal through the ultrasound transmission of the third fundamental wave signal, a fourth reception signal through the ultrasound transmission of the fourth fundamental wave signal, and a fifth reception signal through the ultrasound transmission of the fifth fundamental wave signal, based on a reflection wave acquired through each ultrasound transmission.

With the B-mode processing function 181, the processing circuitry 18 may generate a signal by adding the third reception signal and the fifth reception signal and subtracting the fourth reception signal so that a non-linear signal can be acquired. FIG. 3 shows a non-linear signal as in (H), which represents the resultant signal. The non-linear signal in (H) of FIG. 3 is a harmonic signal from which a fundamental component is removed, and which is composed of a harmonic component. With THI using such a non-linear signal, an image in which artifacts of sidelobes are mitigated can be obtained.

Figure 4:
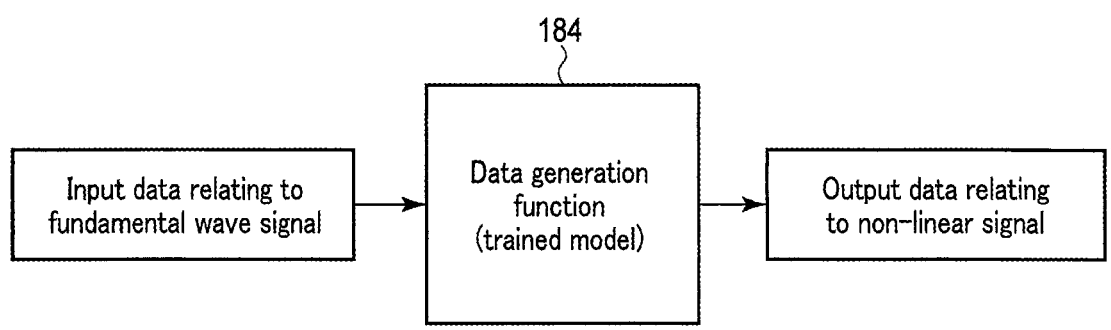
FIG. 4 is a diagram explaining a concept of data input to and output from a data generation function of processing circuitry according to the first embodiment.

FIG. 4 is a diagram explaining the concept of data input to and output from the data generation function 184 of the processing circuitry 18 in the ultrasonic diagnostic apparatus 1 according to the present embodiment. In the ultrasonic diagnostic apparatus 1, the input data based on the fundamental wave signal of the ultrasonic wave transmitted from the ultrasound transmission circuitry 11 is input to the data generation function 184 of the processing circuitry 18. The input data may be a reception signal received by the ultrasound reception circuitry 12 in response to the fundamental wave signal of an ultrasonic wave transmitted from the ultrasound transmission circuitry 11. The input data may be a first reception signal from the ultrasound transmission of the first fundamental wave signal illustrated as (A) in FIG. 2, or a fourth reception signal from the full CH transmission of the fundamental wave signal illustrated as (B) in FIG. 3. That is, the input data is a reception signal acquired through one ultrasound transmission of a fundamental wave signal. The processing circuitry 18 applies a trained model for generating output data based on a non-linear signal of an ultrasonic wave to the input data based on the fundamental wave signal and generates output data based on a non-linear signal, without PM or AM transmission or reception. The output data based on a non-linear signal is output from the data generation function 184 of the processing circuitry 18. Training with the data generation function will be described in detail later.

FIG. 5 is a diagram explaining the data generation function 184 of the processing circuitry 18. The data generation function 184 may be realized by a convolution neural network (CNN). Although processing at a 4-layered CNN is described below as an example, the number of layers is not limited. In FIG. 5, each of four arrows denotes a convolutional layer, where input data and output data from four convolutional layers L11, L12, L13, and L14 is illustrated.

Into the first convolutional layer L11, input data (image data) of the number S0 of samples×the number R0 of received rasters is input. Here, the number S0 of samples corresponds to the image height of a B-mode image generated by the processing circuitry 18, and the number R0 of received rasters corresponds to the image width. With the data generation function 184, the processing circuitry 18 implements convolution processing on the signal, using the number N1 of filters of kernel size K0×L0, and thereby generates signals in which the number of samples and the number of rasters are thinned out to S1 and R1, respectively. In other words, S0>S1 and R0>R1.

The number of signals, which corresponds to the number S1 of samples×the number R1 of rasters, are input to the second convolutional layer L12. With the data generation function 184, the processing circuitry 18 implements convolution processing on each of the signals, using the number N2 of filters of kernel size K1×L1, and thereby generates signals in which the number of samples and the number of rasters are thinned out to S2 and R2, respectively. In other words, S1>S2 and R1>R2.

The number of signals, which corresponds to the number S2 of samples×the number R2 of rasters, are input to the third convolutional layer L13. With the data generation function 184, the processing circuitry 18 implements inverse convolution processing on each of the signals, using the number N3 of filters of kernel size K3×L3, and thereby generates signals in which the number of samples and the number of rasters are increased to S3 and R3. In other words, S2<S3 and R2<R3.

The number of signals, which corresponds to the number S3 of samples×the number R3 of rasters, are input to the fourth convolutional layer L14. With the data generation function 184, the processing circuitry 18 implements inverse convolution processing on each of the signals using a filter of the kernel size K3×L3, thereby generating signals in which the number of samples and the number of rasters are increased to S4 and R4, respectively. In other words, S3<S4 and R3<R4. Here, S4=S0 and R4=R0. The number of signals corresponding to the number S0 of samples×the number R0 of rasters, or in other words, output data of the same size as the input data, is output from the fourth convolutional layer L14.

In the above explanation, the CNN includes four convolutional layers L11, L12, L13, and L14 as the data generation function 184, but the number of convolutional layers and the types of layers can be freely determined. Furthermore, the method of machine learning is not limited to CNN, but a different machine learning method may be adopted.

Figure 6:
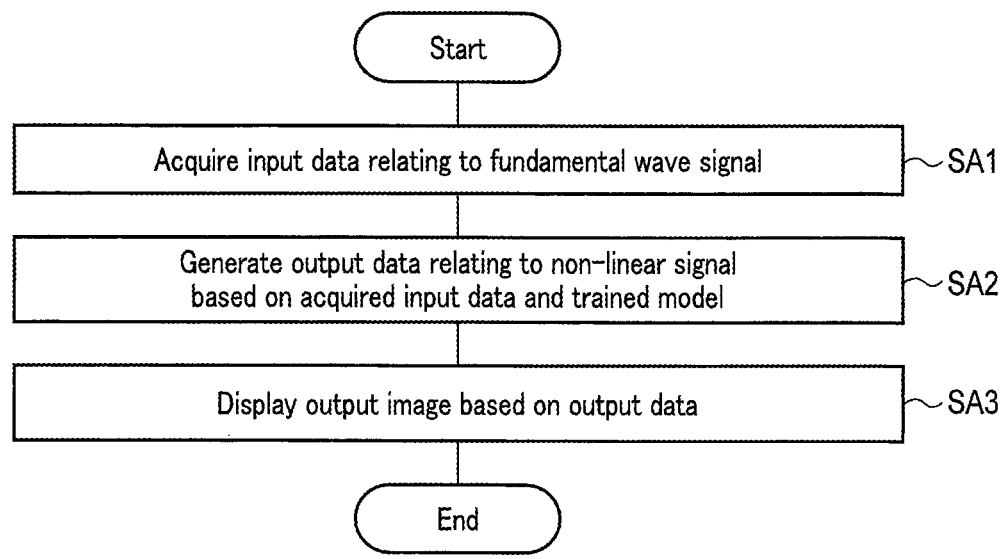
FIG. 6 is a flowchart of an exemplary operation of the processing circuitry with the data generation function.

FIG. 6 is a flowchart of an exemplary operation of the processing circuitry 18 with the data generation function 184. At step SA1, the processing circuitry 18 acquires input data relating to the fundamental wave signal of the ultrasound reception beam. At step SA2, the processing circuitry 18 generates output data relating to a non-linear signal, based on the acquired input data and trained model. At step SA3, the processing circuitry 18 displays on the display device 40 an output image based on the output data.

Figure 7:
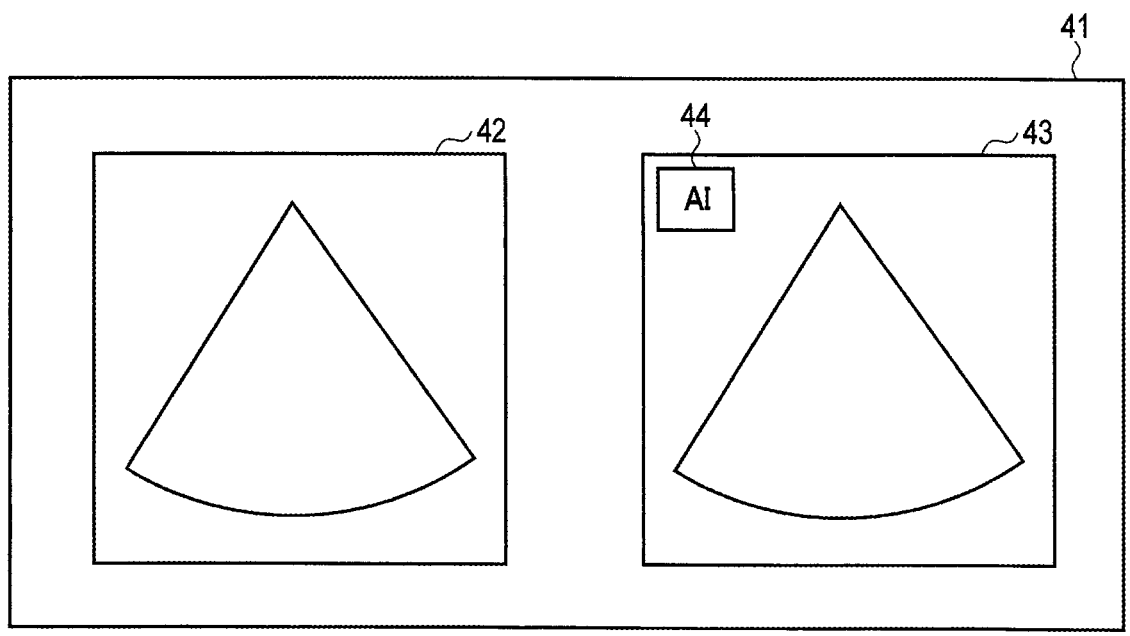
FIG. 7 is a diagram showing an exemplary screen displayed on a display device based on output data.

FIG. 7 is a diagram showing an example of a display screen 41 displayed on the display device 40 based on the above output data. In FIG. 7, a B-mode image 42 created based on the B-mode image data by the B-mode processing function 181 of the processing circuitry 18 and an image 43 created by the data generation function 184 are displayed side by side on the display device 40. The B-mode image 42 and the image 43 based on the data generation function 184 are displayed on the display device 40 in an easily recognizable manner. In FIG. 7, an indication 44 "AI" is attached to the image 43 based on the data generation function 184. The display does not always have to show two side-by-side images, but may show only the image 43 and indication 44.

As explained above, in the ultrasonic diagnostic apparatus 1 according to the present embodiment, the processing circuitry 18 includes a generation section that, using input data based on a fundamental wave signal of an ultrasonic wave, generates output data based on a non-linear signal of an ultrasonic wave. By entering the input data that has been acquired through an examination based on the fundamental wave signal of the ultrasonic wave into the generation section, the generation section generates output data based on the non-linear signal. In this manner, ultrasonic diagnostic image data can be generated with reduced sidelobe artifacts. An ultrasonic image of a quality nearly as high as that of a THI ultrasonic image can be obtained, based on the reception data relating to the transmission of the fundamental wave signals and acquired through fewer ultrasound transmissions in comparison with the conventional technique. For example, according to the PM illustrated in FIG. 2, THI is conducted with two ultrasound transmissions relating to a fundamental wave signal. In contrast, according to the present embodiment, an ultrasonic image of a quality as high as the quality by THI can be obtained through one ultrasound transmission of a fundamental wave signal, which can double the frame rate. With the reduced number of ultrasound transmissions in comparison with the conventional PM or AM technique using a non-linear signal, the frame rate can be increased.

According to the present embodiment, even when the ultrasound transmission of a fundamental wave signal is conducted, an image of nearly the bearing resolution of an image using a non-linear signal can be obtained from the reception data based on the fundamental wave signal.

(Example of Trained Model Generation)

A trained model according to the present embodiment is a machine learning model that has been trained through machine learning in accordance with a model training program based on the training data. The trained model according to the present embodiment is provided with a function of outputting an ultrasonic image based on a non-linear signal in response to the input of an ultrasonic image based on a fundamental wave signal. Here, the training data includes input data that is an ultrasonic image based on the fundamental wave signal, and supervisory data that is an ultrasonic image based on a non-linear signal.

The generation of a trained model will be explained below by referring to FIGS. 8 to 12.

Figure 8:
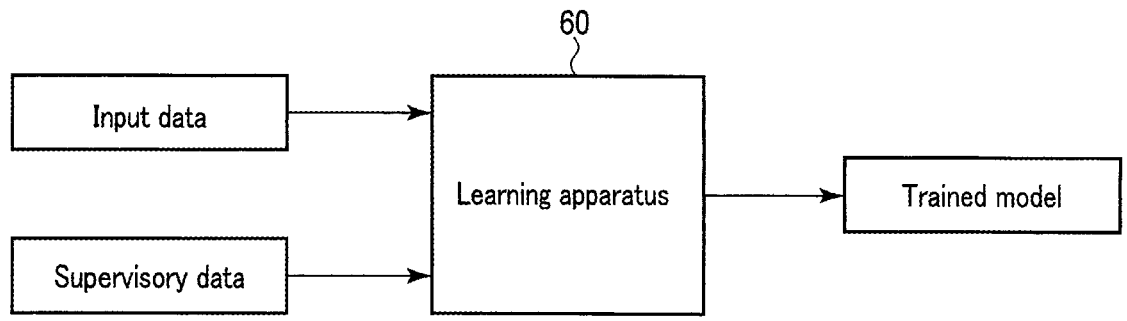
FIG. 8 is a diagram explaining generation of a trained model by a learning apparatus.

FIG. 8 is a diagram explaining generation of a trained model according to the present embodiment. The trained model is generated by a learning apparatus 60. The learning apparatus 60 includes a machine learning model such as the above CNN. The learning apparatus 60 performs learning (supervised learning) based on input data and supervisory data on an ultrasonic examination at the same position of a subject, and thereby generates a trained model. That is, a trained model is a trained machine learning model. If the ultrasonic diagnostic apparatus 1 is equipped with a function of generating a trained model, the ultrasonic diagnostic apparatus 1 may be referred to as a learning apparatus 60.

Figure 9:
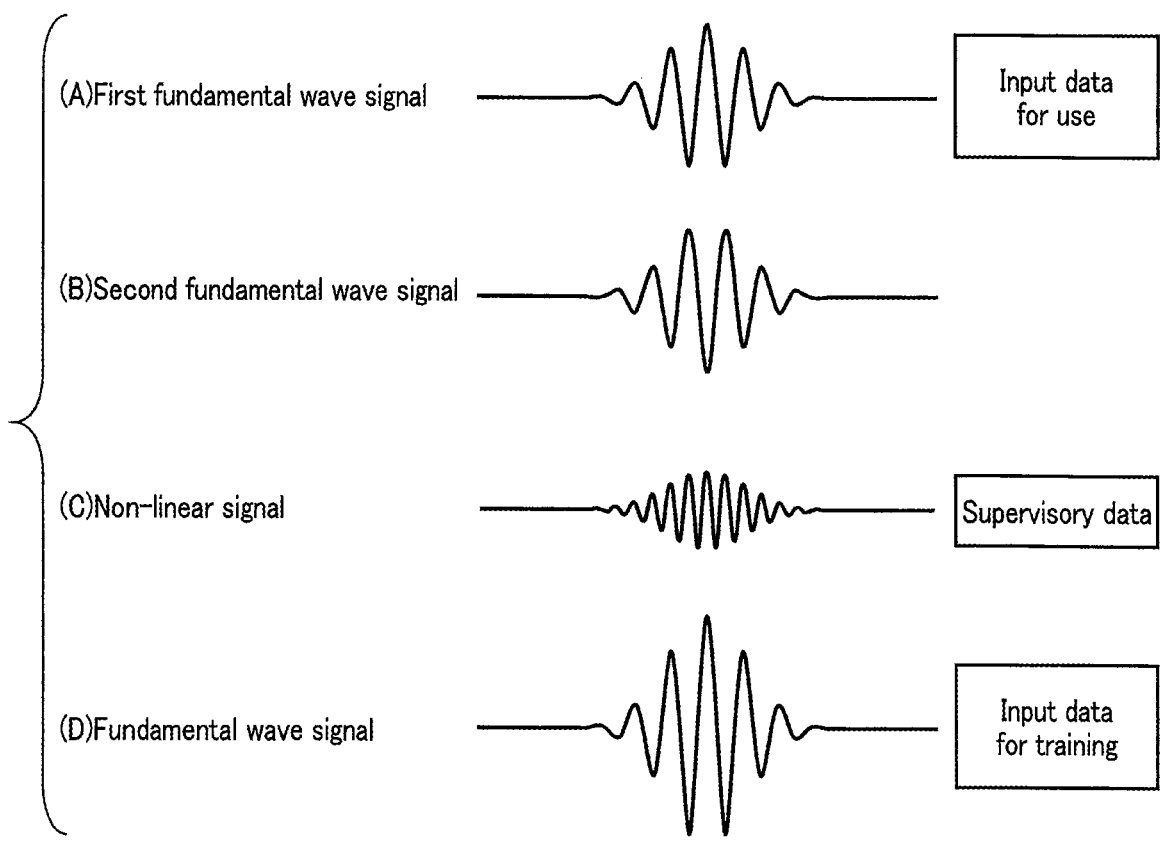
FIG. 9 is a diagram showing an exemplary phase modulation in relation to the generation and use of a trained model.
Figure 10:
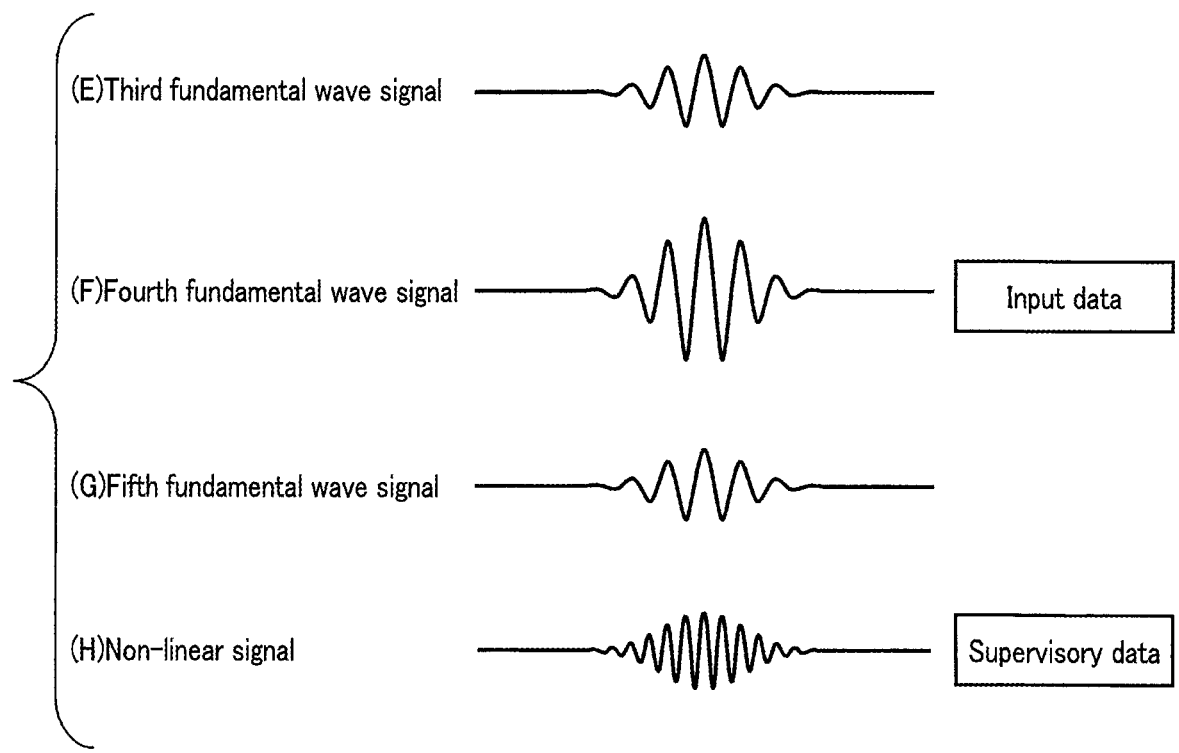
FIG. 10 is a diagram showing an exemplary amplitude modulation in relation to the generation and use of a trained model.

The input data and supervisory data used by the learning apparatus 60 for machine learning will be explained below with reference to FIGS. 9 and 10. FIG. 9 is a diagram showing an exemplary phase modulation in relation to generation and use of a trained model. FIG. 10 is a diagram showing an exemplary amplitude modulation in relation to the generation and use of a trained model. The waveforms corresponding to the signals illustrated in FIGS. 9 and 10 are the same as FIGS. 2 and 3.

For example, the learning apparatus 60 adopts, as input data for training, a subtraction signal acquired from a difference between the first reception signal through the ultrasound transmission of the first fundamental wave signal and the second reception signal through the ultrasound transmission of the second fundamental wave signal, as illustrated as (D) in FIG. 9. As mentioned earlier, this subtraction signal is a fundamental wave signal composed of a fundamental component from which harmonic components are removed. Moreover, the learning apparatus 60 adopts, as supervisory data, an add signal acquired from a sum of the first reception signal through the ultrasound transmission of the first fundamental wave signal and the second reception signal through the ultrasound transmission of the second fundamental wave signal, as illustrated as (C) in FIG. 9. This add signal is, as mentioned earlier, a non-linear signal composed of harmonic components from which a fundamental component is removed.

The subtraction signal is adopted as input data for training in order to bring its S/N ratio to the same level as that of the add signal of the supervisory data. As input data for training, the first reception signal or second reception signal may be adopted. That is, fundamental wave signals will sufficiently serve as the input data for training.

As explained with reference to FIG. 4, the input data that is input to the trained model (data generation function 184) during the use of the ultrasonic diagnostic apparatus 1 is the first reception signal acquired through the ultrasound transmission of a first fundamental wave signal, as illustrated as (A) in FIG. 9. That is, the input data during the use is a fundamental wave signal acquired through a single ultrasound transmission.

Alternatively, the learning apparatus 60 may adopt the fourth reception signal acquired through the full CH transmission as input data (input data during training and input data during its use), as illustrated as (F) in FIG. 10. The fourth reception signal is a reception signal composed of a fundamental component relating to the transmission of the fourth fundamental wave signal, as mentioned earlier. The learning apparatus 60 further adopts, as supervisory data, a signal acquired by subtracting the fourth reception signal acquired through the full CH transmission from the sum of the third reception signal acquired through the even-numbered CH transmission and the fifth reception signal acquired through the odd-numbered CH transmission, as illustrated as (H) in FIG. 10. As mentioned earlier, this signal is a non-linear signal of a harmonic component.

In the AM of FIG. 10, instead of two ultrasound transmissions, three ultrasound transmissions are adopted as a sequence for generating supervisory data. In order to avoid a non-linear response of the ultrasound transmission circuitry 11, the ultrasound transmission circuitry 11 conducts the first-time ultrasound transmission as even-numbered CH transmissions without changing the transmission acoustic pressure, thereby realizing the reduction of the transmission acoustic pressure to half the second-time full CH transmission. Furthermore, the ultrasound transmission circuitry 11 conducts the third-time ultrasound transmission as an odd-numbered CH transmission and adds the third reception signal acquired through the first-time ultrasound transmission and the fifth reception signal acquired through the third-time ultrasound transmission at the processing circuitry 18. The resultant signal is the same as the fourth reception signal acquired through the full CH transmission, with respect to a linear response signal. By subtracting the two, only a non-linear signal remains ((H) in FIG. 10).

The transmission acoustic pressure of half the acoustic pressure of the full CH transmission may be realized by a transmission method other than the odd-numbered CH transmission or even-numbered CH transmission. The AM through three ultrasound transmissions is explained merely as an example; the AM may be performed through two ultrasound transmissions. For example, a non-linear signal may be acquired by multiplying reception signals of two ultrasound transmissions by a coefficient and subtracting the signals.

Signals in which both the amplitude and phase of a transmission ultrasonic wave are changed, or in other words, signals adopting both the AM and PM, may be used; however, the explanation of such use is omitted here.

FIG. 11 is a diagram showing a specific example of generation of a trained model generated by the learning apparatus 60. In the learning apparatus 60, ultrasonic image data generated based on a fundamental wave signal, for example in (D) of FIG. 9 or (F) of FIG. 10, is input as input data to the machine learning model 61 (CNN). The learning apparatus 60 applies the CNN to the input data relating to the fundamental wave signal, and thereby generates, as explained with reference to FIG. 5, output data relating to a non-linear signal. The output data relating to the non-linear signal is output from the CNN. In the learning apparatus 60, the output data is entered into the evaluation function 62. Furthermore, in the learning apparatus 60, ultrasonic image data generated based on a non-linear signal, for example in (C) in FIG. 9 or (H) in FIG. 10, is entered into the evaluation function 62 as supervisory data. With the evaluation function 62, the learning apparatus 60 evaluates the supervisory data and the output data generated by the machine learning model (CNN) based on the input data. The evaluation function 62 may compare the generated output data with the supervisory data, and correct the coefficients of the CNN (network parameters such as weight and bias) through backpropagation. The evaluation with the evaluation function 62 is fed back to the CNN. The learning apparatus 60 repeats a series of supervised learning operations based on the training data, which is a set of input data and supervisory data acquired with respect to the same position of the subject, for example, until the error between the output data and the supervisory data is smaller than or equal to a predetermined threshold value. The learning apparatus 60 may output the trained machine learning model as a trained model.

FIG. 12 is a flowchart of an exemplary operation of the learning apparatus 60 generating a trained model. At step SB1, the learning apparatus 60 initializes the parameters of the machine learning model. At step SB2, the learning apparatus 60 acquires the input data and supervisory data. At step SB3, the learning apparatus 60 trains the machine learning model in the above described manner, based on the acquired input data and supervisory data. At step SB4, the learning apparatus 60 outputs the trained machine learning model as a trained model.

A trained model needs to be prepared for each type of the ultrasonic probe 20 and for each frequency of the ultrasonic wave used in the ultrasonic probe 20, in accordance with the physical conditions and usage setting of the ultrasonic probe 20 that may be changed when the ultrasonic probe 20 is replaced, or when the frequency of the ultrasonic wave used in the ultrasonic probe 20 is changed. Furthermore, a trained model needs to be prepared in accordance with the maximum depth of field, the number of transmission rasters, the number of reception rasters, or target area such as abdomen, heart, or fetus. The learning apparatus 60 (ultrasonic diagnostic apparatus 1) may output various trained models in advance, for example before the factory shipment.

In the above explanation, it is assumed that the learning apparatus 60 generates a trained model before the factory shipment so that the model can be used on the ultrasonic diagnostic apparatus 1 at the time of an ultrasonic examination. The mode of usage, however, is not limited thereto. The learning apparatus 60 (ultrasonic diagnostic apparatus 1) may perform real-time training at regular ultrasonic examinations conducted on the ultrasonic diagnostic apparatus 1 equipped with the learning apparatus 60. If this is the case, the input data (non-linear signal in (C) of FIG. 9) which serves as training data, and the supervisory data (fundamental wave signal in (D) of FIG. 9) are generated from the first reception signal based on the first fundamental wave signal as illustrated in (A) of FIG. 9 and the second reception signal based on the second fundamental wave signal as illustrated in (B) of FIG. 9, which have been acquired through the PM, and training is thereby performed using this training data. In this manner, the existing trained model can be updated even after the factory shipment.

As explained above, the learning apparatus 60 (CNN, data generation function) according to the present embodiment acquires input data based on a fundamental wave signal of an ultrasonic wave and supervisory data based on a non-linear signal of an ultrasonic wave through at least two ultrasound transmissions, and performs machine learning on the machine learning model based on the input data and supervisory data. The learning apparatus 60 thereby generates a trained model for an ultrasonic diagnostic apparatus that can generate output data based on the non-linear signal of an ultrasonic wave using input data based on the fundamental wave signal of an ultrasonic wave. The at least two ultrasound transmissions are conducted using ultrasonic waves of the same acoustic pressure and phases inverted from each other with respect to the same scan direction (FIG. 9); or otherwise conducted using ultrasonic waves of different acoustic pressures with respect to the same scan direction (FIG. 10). The ultrasonic diagnostic apparatus 1 equipped with this trained model outputs, using the input data based on the fundamental wave signal of an ultrasonic wave, output data based on a non-linear signal, for example an ultrasonic image equivalent to the THI quality, through inference from the results of the machine learning. In the CHI, a non-linear signal can also be detected through the AM, and therefore the same usage mode for the THI is possible for the CHI.

When input data and supervisory data are supplied to the CNN, internal parameters are generated for conversion to supervisory data from the characteristics of the input data. More data items in the data for the machine learning are more preferable; desirably, for example, more than several thousand data items may be incorporated.

In order to obtain more than several thousand data items, efficient obtainment of the input data and supervisory data is important. When biological data is obtained by the ultrasonic diagnostic apparatus 1, the operator holds the ultrasonic probe in hand to scan the living body that is moving. It is therefore impossible to collect data of the exactly same cross section while changing the conditions between the input data and supervisory data with the user interface on the panel, because the living body may move or the hand holding the probe may move. For the machine learning, however, the input data and supervisory data need to be obtained from a precisely identical cross section, position of the living body organ, and time phase of cardiac pulsation, requiring precision on a scale of a wavelength.

In the learning apparatus 60 according to the present embodiment, the input data and supervisory data acquired at the time of training are a fundamental wave signal and non-linear signal with respect to the same cross section of the subject. Thus, a trained model can be efficiently generated. The generated trained model generates, using the input data based on the fundamental wave signal received at the scan position, output data based on the non-linear signal received at this scan position.

Application Examples

According to the first embodiment, ultrasonic image data is mainly used as input data and output data (or supervisory data). That is, according to the first embodiment, the processing circuitry 18 with the data generation function 184 generates, using input data based on ultrasonic image data derived from a fundamental wave signal, output data based on ultrasonic image data derived from a non-linear signal. In an application example according to the first embodiment, the use of the data processed in a certain section of the processing circuitry 18 is explained.

FIG. 13 is a diagram explaining the data flow from the ultrasound reception circuitry 12 to the processing circuitry 18 and to the display device 40. The B-mode processing function 181 of the processing circuitry 18 includes a detection function 1811 and logarithmic compression function 1812. The data received by the ultrasound reception circuitry 12 is processed by the processing circuitry 18 so that an image is displayed on the display device 40.

With the detection function 1811 of the B-mode processing function 181 in the processing circuitry 18, the received data is subjected to the detection processing. The processed data is sent from the detection function 1811 to the logarithmic compression function 1812. Then, with the logarithmic compression function 1812, the sent data is subjected to the logarithmic compression processing. The processed data is sent from the logarithmic compression function 1812 to the image generation function 183. With the image generation function 183, the sent data is subjected to the image generation processing through coordinate conversion so that B-mode image data is generated. The B-mode image data is sent from the image generation function 183 to the display device 40. The display device 40 displays a B-mode image under the control of the display control function 185 of the processing circuitry 18.

According to these application examples, the processing circuitry 18 implements the data generation function 184 at some point in FIGS. 14, 16 and 17. The processing circuitry 18 may implement the data generation function 184 at multiple sections.

FIG. 14 is a diagram showing an example of part of the implementation of the data generation function 184. According to FIG. 14, the data generation function 184 is applied to a signal (IQ signal or RF signal, as discussed later) subjected to the beam-forming by the beam former 127 of the ultrasound reception circuitry 12, which is described later. That is, with the data generation function 184, the processing circuitry 18 generates, using input data based on the reception signal in response to the fundamental wave signal, output data based on the reception signal in response to the non-linear signal. The data generated by the application of the data generation function 184 is sent to the detection function 1811 in the processing circuitry 18.

Figure 15:
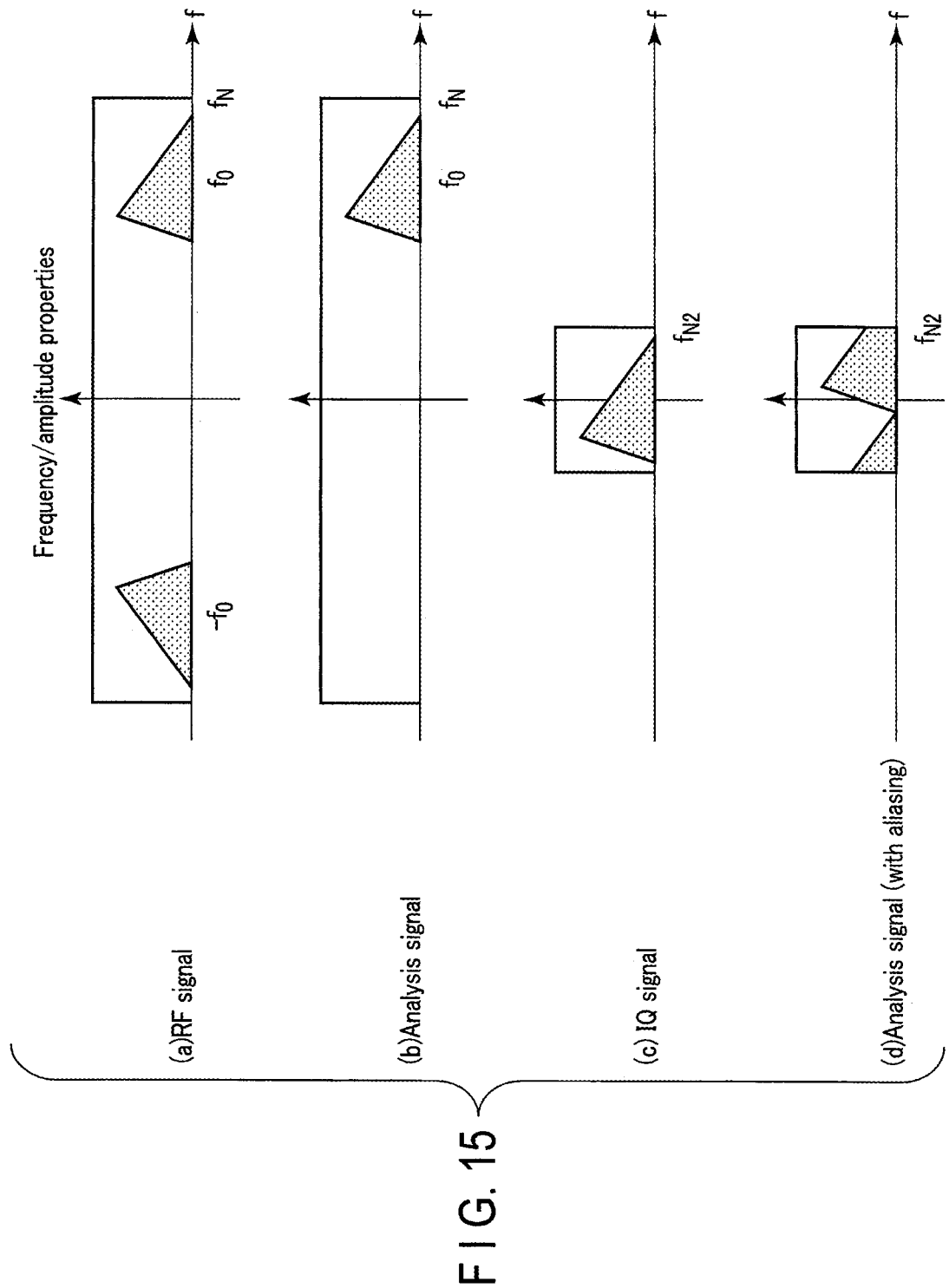
FIG. 15 is a diagram explaining multiple signals processed by the ultrasound reception circuitry and the relationship of frequency and amplitude properties of the signals.

The signals handled by the ultrasound reception circuitry 12 are explained. FIG. 15 is a diagram explaining multiple signals processed by the ultrasound reception circuitry 12 and the relationship of their frequency and amplitude properties. The signals may include an RF signal, analysis signal, IQ signal, and analysis signal with aliasing (hereinafter may be referred to as aliasing analysis signal). These signals are used as input data.

The frequency and amplitude properties of an RF signal are illustrated in (a) of FIG. 15. An RF signal is acquired by directly A/D converting a signal that is output from each channel of the ultrasonic probe 20 and a signal that is output from each preamplifier of a preamplifier group, which will be described later.

The frequency and amplitude properties of an analysis signal are illustrated in (b) of FIG. 15. An analysis signal is acquired from a signal of a positive frequency band extracted by filtering the RF signal.

The frequency and amplitude properties of an IQ signal are illustrated in (c) of FIG. 15. An IQ signal is acquired by mixing the analysis signal with a center frequency $f_0$. The IQ signal corresponds to a signal output from each demodulator of a demodulator group, which will be described later, and a signal output from the beam former.

The frequency properties of an aliasing analysis signal are illustrated in (d) of FIG. 15. An aliasing analysis signal is acquired by applying the following equation (1) to an IQ signal of a low sampling frequency (Nyquist frequency fN2) indicated in (c) of FIG. 15. Here, $f_0$ represents a mixing frequency when generating an IQ signal from the RF signal.

$$Ana(t)=IQ(t)e^{j2\pi f_0 t} \quad \text{Equation (1)}$$

In the example of FIG. 14, the signal received by the processing circuitry 18 with the data generation function 184 from the ultrasound reception circuitry 12 may be the IQ signal after beam forming as illustrated in (c) of FIG. 15. With regard to the IQ signal that is a complex number, all of the calculations at the data generation function 184 are conducted with complex numbers. For instance, when the coefficient is a real number and I and Q are to be independently handled, the input data to the first convolutional layer includes two items of data with the number S0 of samples× the number R0 of rasters. Alternatively, in place of the IQ signal, an analysis signal as indicated in (b) of FIG. 15 or an aliasing analysis signal as indicated in (d) of FIG. 15 may be adopted so that the phase of the wave that changes in the depth direction can be included in the information.

When beam forming is performed by the ultrasound reception circuitry 12 with an RF signal, the processing circuitry 18 acquires an RF signal as indicated in (a) of FIG. 15, with the data generation function 184. In some cases when performing the beam forming with an IQ signal, it may be preferable to use the CNN after converting the IQ signal to an RF signal. For instance, most of the existing CNN frameworks can handle real numbers only. However, even if the original signal is an IQ signal, the existing frameworks are usable by converting the IQ signal to an RF signal.

To convert the IQ signal received by the processing circuitry 18 from the ultrasound reception circuitry 12 to an RF signal, first, the IQ signal IQ(t) is interpolated to acquire a signal IQ2($t$) of a sampling frequency such that the frequency band of the original RF signal can be covered. The conversion of the IQ signal IQ2($t$) to an RF signal RF(t) can be represented by the following equation (2). Here, $f_0$ represents the mixing frequency when generating an IQ signal from the RF signal, and Re[ ] represents extraction of a real number only.

$$RF(t)=Re[IQ2(t)e^{j2\pi f_0 t}] \quad \text{Equation (2)}$$

FIG. 16 is a diagram showing an example of part of the implementation of the data generation function 184. According to FIG. 16, the data generation function 184 is applied to the data subjected to the detection processing with the detection function 1811 of the processing circuitry 18. That is, the processing circuitry 18 generates, using the input data based on a detection signal derived from a fundamental wave signal, output data based on a detection signal derived from a non-linear signal, with the data generation function 184. Since the data is a signal of a real number, processing similar to ordinary processing for a gray-scale B-mode image can be performed. The data generated by applying the data generation function 184 is sent to the logarithmic compression function 1812 in the processing circuitry 18.

FIG. 17 is a diagram showing an example of part of the implementation of the data generation function 184. According to FIG. 17, the data generation function 184 is applied to the data subjected to the logarithmic compression processing with the logarithmic compression function 1812 of the processing circuitry 18. That is, the processing circuitry 18 generates, using the input data based on a logarithmic compression signal derived from a fundamental wave signal, output data based on a logarithmic compression signal derived from a non-linear signal, with the data generation function 184. Again, since the data is a real number signal, processing similar to ordinary processing for a gray-scale B-mode image can be performed. The data generated by the application of the data generation function 184 is sent to the image generation function 183 in the processing circuitry 18.

According to the first embodiment, as described above, the processing circuitry 18 implements the data generation function 184 with the trained model on any of the IQ signal, RF signal, analysis signal or aliasing analysis signal, signal after the detection, signal after the logarithmic compression, and an ultrasonic image after the coordinate conversion received from the ultrasound reception circuitry 12.

Second Embodiment

According to the above first embodiment and application example of the first embodiment, the use of data subjected to beam forming has been mainly explained as the input data and output data (or supervisory data). According to the second embodiment, the use of the data before being subjected to beam forming will be explained.

FIG. 18 is a block diagram illustrating an exemplary configuration of an ultrasonic diagnostic apparatus 1 according to the second embodiment. In the following explanation, differences between the first embodiment and the second embodiment will be focused on, and the structures and operations similar to the first embodiment will be omitted.

The ultrasound reception circuitry 12 according to the second embodiment is provided with a pre-processing function 121, a data generation function 122, and a post-processing function 123. The pre-processing function 121 is configured to pre-process the data to be input to the data generation function 122 into a format suitable for the processing of the data generation function 122. The data generation function 122 basically corresponds to the data generation function 184 of the processing circuitry 18 according to the first embodiment. The post-processing function 123 is configured to perform post-processing on the data generated by the data generation function 122 into a format suitable for the subsequent processing. The processing circuitry 18 of the present embodiment does not include a data generation function.

Figure 19:
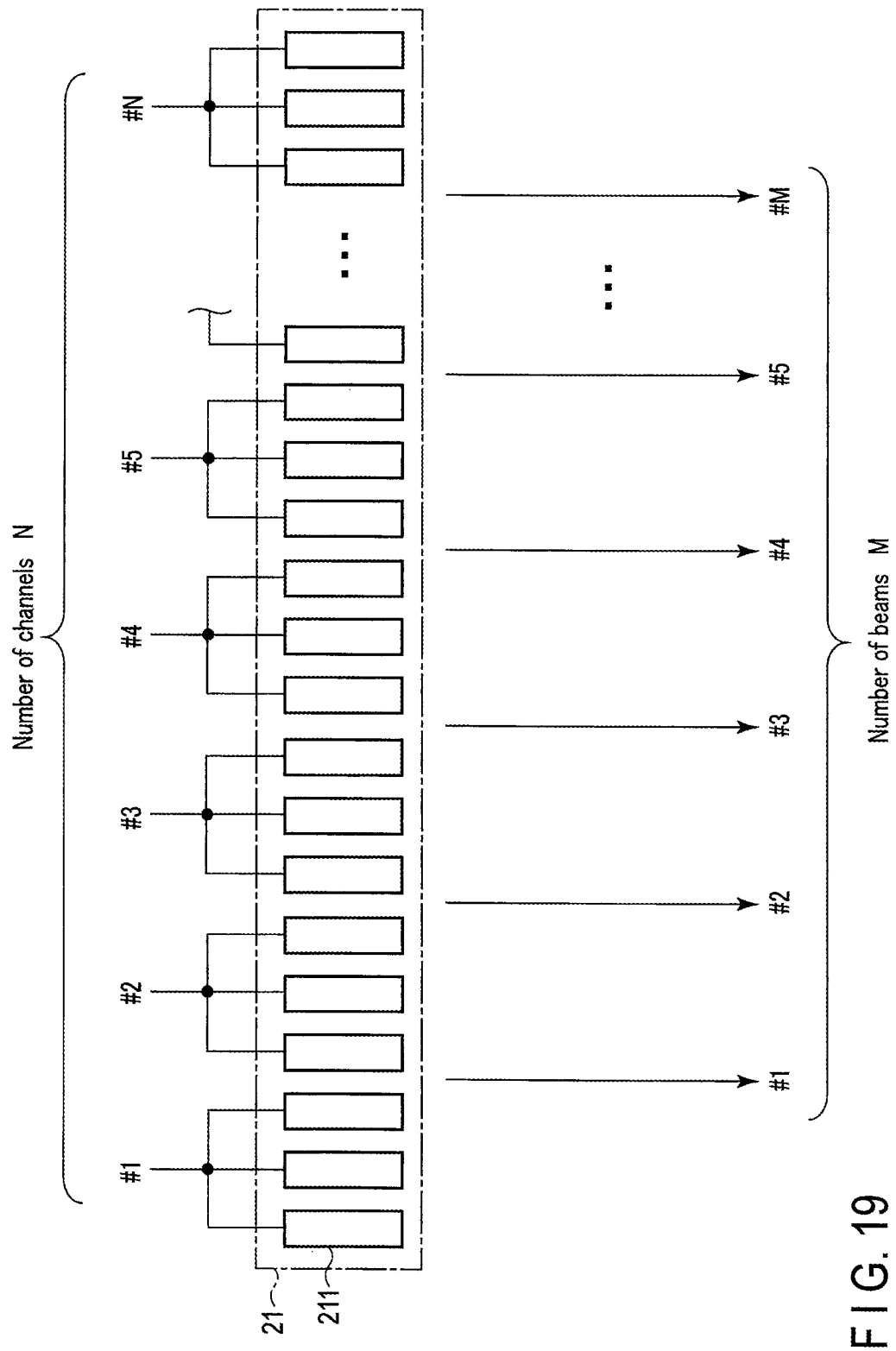
FIG. 19 is a diagram explaining the concept of the number of channels and the number of beams in an ultrasonic probe.

FIG. 19 is a diagram explaining the concept of the numbers of channels and beams of an ultrasonic probe 20. The ultrasonic probe 20 includes a probe section 21 composed of multiple ultrasonic vibrators 211. The ultrasonic vibrators 211 are divided into sets of several ultrasonic vibrators, with each of the sets forming a channel. In other words, each channel includes one or more ultrasonic vibrators 211. By the ultrasound transmission circuitry 11 driving the channels at the same timing, the ultrasonic probe 20 performs the ultrasound transmission.

FIG. 19 shows N channels from #1 to #N. If the ultrasound transmission is to be performed by driving two channels at the same timing, the ultrasound transmission circuitry 11 drives the channels #1 and #2 at the same timing. When the channels #1 and #2 are driven at the same timing, the composite surface of the ultrasonic waves are created, thereby forming a beam #1. Similarly, the ultrasound transmission circuitry 11 drives the channels #2 and #3 at the same timing to form a beam #2. In this manner, ultrasound transmissions from two adjacent channels form one beam. FIG. 19 shows M beams from #1 to #M. The number of channels driven at the same timing is not limited to two, but may be three or more. The aforementioned "full CHs" represents all the channels that are being driven at the same timing. The "odd-numbered CHs" represents channels that are odd-numbered (e.g., #1, #3, . . . , #N-1), and the "even-numbered CHs" represents channels that are even-numbered (e.g., #2, #4, . . . , #N).

FIG. 20 is a block diagram showing an exemplary structure of the ultrasound reception circuitry 12 and processing circuitry 18. The ultrasound reception circuitry 12 includes a preamplifier group 124, an A/D converter group 125, a demodulator group 126, and a beam former 127. The preamplifier group 124 includes preamplifiers 124-1, 124-2, . . . , and 124-N. The A/D converter group 125 includes A/D converters 125-1, 125-2, . . . , and 125-N. The demodulator group 126 includes demodulators 126-1, 126-2, . . . , and 126-N.

Reception signals are entered into the preamplifiers 124-1 to 124-N through the channels #1 to #N. The preamplifiers 124-1 to 124-N amplify the respective reception signals. The reception signals amplified by the preamplifiers 124-1 to 124-N are entered into the A/D converters 125-1 to 125-N. The A/D converters 125-1 to 125-N convert the amplified reception signals from analog signals to digital signals. The converted reception signals are entered into the demodulators 126-1 to 126-N. The demodulators 126-1 to 126-N demodulate the converted reception signals. The demodulated reception signals are entered into the beam former 127. The beam former 127 performs beam forming on the demodulated reception signals. The reception signals subjected to the beam forming are sent to the processing circuitry 18.

Figure 21:
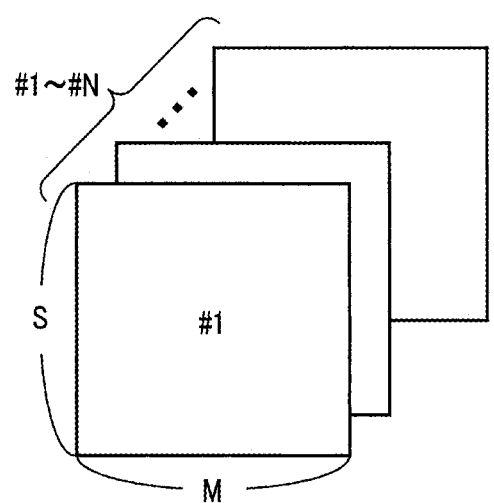
FIG. 21 is a diagram showing exemplary input data that is input to the data generation function.

FIG. 21 is a diagram showing exemplary input data that is input to the data generation function 122. The data generation function 122 may be realized by the CNN including four convolutional layers L11, L12, L13, and L14. To the first convolutional layer L11, input data (signals) having the number S of samples×the number M of reception beams for each channel of the number N of channels of is input. Here, the number S of samples represents the height of a B-mode image generated by the processing circuitry 18, and the number M of reception beams represents the width of the image. The input data of FIG. 21 is processed by the pre-processing function 121.

FIG. 22 is a diagram showing an example of part of the implementation of the data generation function 122. In FIG.

22, the digital signals converted from analog signals by the A/D converter group 125 are entered into the pre-processing function 121 of the ultrasound reception circuitry 12. With the pre-processing function 121, the ultrasound reception circuitry 12 processes (pre-processes) the digital signals as matrix data one axis of which corresponds to the depth direction of the scan area and the other axis of which corresponds to the transmission beam direction. The pre-processed signals are entered into the data generation function 122. The data generation function 122 is applied to the pre-processed signals. That is, with the data generation function 122, the ultrasound reception circuitry 12 generates, using input data based on the matrix data derived from the fundamental wave signal, output data based on the matrix data derived from the non-linear signal. The signals generated through the application of the data generation function 122 are entered into the post-processing function 123 of the ultrasound reception circuitry 12. With the post-processing function 123, the ultrasound reception circuitry 12 post-processes the signals. The post-processed signals are entered into the demodulator group 126.

Figure 23:
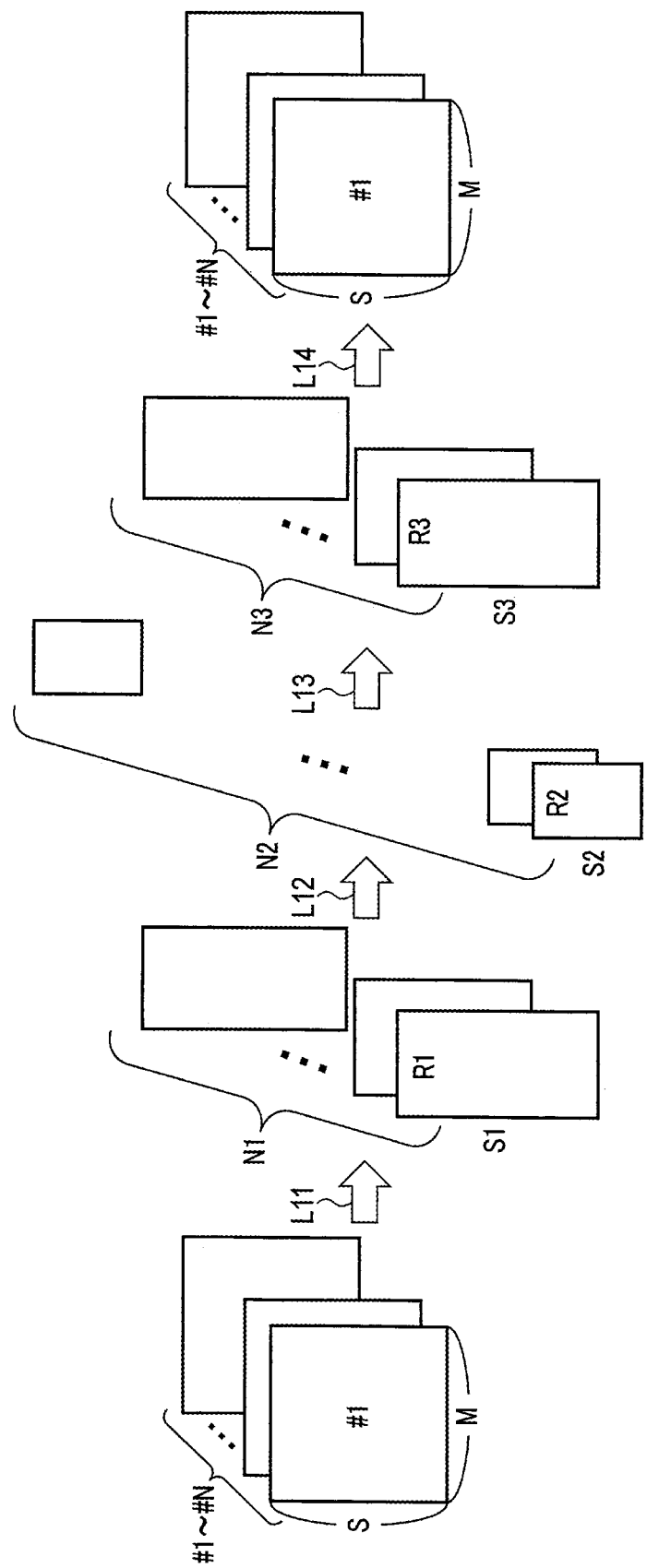
FIG. 23 is a diagram explaining the data generation function of the ultrasound reception circuit.

FIG. 23 is a diagram explaining the data generation function 122 of the ultrasound reception circuitry 12. The data generation function 122 may be realized by the CNN. Although processing at a 4-layered CNN is described below as an example, the number of layers is not limited. In FIG. 23, with each of four arrows indicating a convolutional layer, the input data and data that is output from the four convolutional layers L11, L12, L13, and L14 are illustrated. In FIG. 23, only the data through channel #1 is illustrated as the data output from a convolutional layer, and the data through channels #2 to #N is omitted.

Into the first convolutional layer L11, input data (signals) having the number S of samples×the number M of beams for each channel of the number N of channels is input. With regard to the data of channel #1, the ultrasound reception circuitry 12 performs convolution processing on the signals with the data generation function 122, using the number N1 of filters of the kernel size K0×L0. The ultrasound reception circuitry 12 thereby generates a signal with its number of samples and beams thinned to S1 and R1, respectively, or in other words, with S0>S1 and M>R1.

Into the second convolutional layer L12, the number of signals corresponding to the number S1 of samples×the number R1 of beams are input. With the data generation function 122, the ultrasound reception circuitry 12 implements convolution processing on each of the signals, using the number N2 of filters of kernel size K1×L1, and thereby generates a signal with its numbers of samples and beams thinned to S2 and R2, respectively, or in other words, with S1>S2 and R1>R2.

Into the third convolutional layer L13, the number of signals corresponding to the number S2 of samples×the number R2 of beams are input. With the data generation function 122, the ultrasound reception circuitry 12 implements inverse convolution processing onto each of the signals, using the number N3 of filters of the kernel size K2×L2, and thereby generates a signal with its numbers of samples and beams increased to S3 and R3, respectively, or in other words, with S2<S3 and R2<R3.

Into the fourth convolutional layer L14, the number of signals corresponding to the number S3 of samples×the number R3 of beams are input. With the data generation function 122, the ultrasound reception circuitry 12 implements inverse convolution processing onto each of the signals using the number N of filters of the kernel size K3×L3, and thereby generates a signal with its numbers of samples and beams increased to S and M, respectively, or in other words, with S3<S and R3<M. Thereafter, a signal of the number S of samples×the number M of beams for each channel of the number N of channels is output from the fourth convolutional layer L14, or in other words, the output data of the same size as the input data is output.

In the above explanation, a CNN including four convolutional layers has been discussed as the data generation function 122, but the number of convolutional layers and the types of layers can be freely determined. Furthermore, the method of machine learning is not limited to the CNN, but a different machine learning method may be adopted. Two-dimensional data is adopted here as input data; however, three-dimensional data is also adoptable. For three-dimensional data, a 3D CNN is applied to process the data.

FIG. 24 is a flowchart of an exemplary operation of the ultrasound reception circuitry 12 with the data generation function 122. At step SC1, the ultrasound reception circuitry 12 acquires reception data relating to the fundamental wave signal of an ultrasound reception beam. At step SC2, the ultrasound reception circuitry 12 implements the pre-processing based on the reception data to generate input data. At step SC3, the ultrasound reception circuitry 12 generates output data relating to a non-linear signal, based on the generated input data and trained model. At step SC4, the ultrasound reception circuitry 12 implements the post-processing on the output data and thereby generates the processed reception data.

FIG. 25 is a flowchart of an exemplary operation of the learning apparatus 60 generating a trained model. At step SD1, the learning apparatus 60 initializes the parameters of the machine learning model. At step SD2, the learning apparatus 60 acquires the input data and supervisory data. At step SD3, the learning apparatus 60 trains the machine learning model, based on the acquired input data and supervisory data. At step SD4, the learning apparatus 60 outputs the trained machine learning model as a trained model.

The input data that is input to the data generation function 122 in FIG. 21 is explained as having the number S of samples×the number M of reception beams for each channel of the number N of channels; however, for example as illustrated in FIG. 26, the input data may include the number S of samples×the number N of channels for each beam of the number M of reception beams. Even for this case, the data can be generated in the same processing as the one in FIG. 23.

According to the present embodiment, the ultrasound reception circuitry 12 includes the data generation function 122. The ultrasound reception circuitry 12 implements the data generation function 122 at some point in FIG. 22 or 27. The data generation function 122 may be implemented at multiple points. An exemplary data flow in the ultrasound reception circuitry 12 will be explained below by referring to FIG. 27.

FIG. 27 is a diagram showing an example of part of the implementation of the data generation function 122. In FIG. 27, a signal demodulated by the demodulator group 126 is entered into the pre-processing function 121 of the ultrasound reception circuitry 12. With the pre-processing function 121, the ultrasound reception circuitry 12 processes (pre-processes) the demodulated signal as matrix data one axis of which corresponds to the depth direction of the scan area and the other axis of which corresponds to the transmission beam direction. The pre-processed reception signal is entered into the data generation function 122. The data generation function 122 is applied to the pre-processed signal. That is, with the data generation function 122, the ultrasound reception circuitry 12 generates, using input data based on the matrix data derived from a fundamental wave signal, output data based on the matrix data derived from a non-linear signal. The signal generated through the application of the data generation function 122 is entered into the post-processing function 123 in the ultrasound reception circuitry 12. With the post-processing function 123, the ultrasound reception circuitry 12 post-processes the signal. The post-processed signal is entered into the beam former 127.

In the example of FIG. 22, the signal that is input to the data generation function 122 is an RF signal of a real number. In the example of FIG. 27, the signal input to the data generation function 122 is an IQ signal of a complex number. Although the example of FIG. 27 differs in this regard, the same data generation function 122 as the one explained with reference to FIG. 23 can be used. That is, the data generation can be realized in the same manner by performing all the computations with complex numbers. The IQ signal has a narrower frequency band than an RF signal, which allows for a lower sampling frequency and a smaller number of samples. As a result, the kernel size in the sample direction can be reduced with respect to the example of FIG. 22, and thus the amount of calculation can be reduced. Each calculation that involves a complex number, however, requires a longer time.

If the coefficient is a real number, an IQ signal can be regarded as independent I and Q signals. The I and Q signals are divided in the channel direction, which doubles the number of channels but allows for all the calculations implemented with real numbers.

As modification example 1 relating to a signal to be processed with the data generation function 122, an analysis signal may be adopted in place of an IQ signal of the baseband signal. The relationship between the analysis signal Ana(t) and IQ signal IQ(t) is expressed in the above equation (1). With an analysis signal in place of an IQ signal, the phase of a wave that varies in the depth direction can be further expressed. Thus, the same result as when adopting an RF signal can be achieved. If analysis signals are adopted for input data and supervisory data during the training, the input data is converted to an analysis signal at the time of use so as to acquire inference data of the analysis signal, and then the process of conversion to an IQ signal is performed.

As modification example 2 relating to a signal to be processed with the data generation function 122, an aliasing analysis signal (see (d) in FIG. 15) may be adopted in place of an IQ signal of the baseband signal. The frequency band of an analysis signal is the same as the frequency band of the RF signal on the positive side ((a) in FIG. 15). For this reason, a high sampling frequency is required. If Equation (1) is applied to an IQ signal of a sampling frequency (Nyquist frequency $f_{N2}$) as low as the one illustrated in (c) of FIG. 15, a signal as illustrated in (d) of FIG. 15 can be acquired. This signal can be interpreted as being in an aliasing state when sampling the analysis signal of the Nyquist frequency $f_N$ in (b) of FIG. 15 at a Nyquist frequency $f_{N2}$. Although the frequency band of the signal is the same baseband as an IQ signal, which is a narrow band, the phase of the signal is maintained at the same state as the original analysis signal. Thus, the phase of the wave that varies in the depth direction can be maintained. This realizes the same result with a low sampling frequency, as when adopting an RF signal or analysis signal, and lowers the amount of calculation. When aliasing analysis signals are adopted for input data and supervisory data during the training, the processing circuitry 18 performs, at the time of use, processing for converting an analysis signal to an aliasing analysis signal to acquire data, and then converting this data to IQ data.

Third Embodiment

Figure 28:
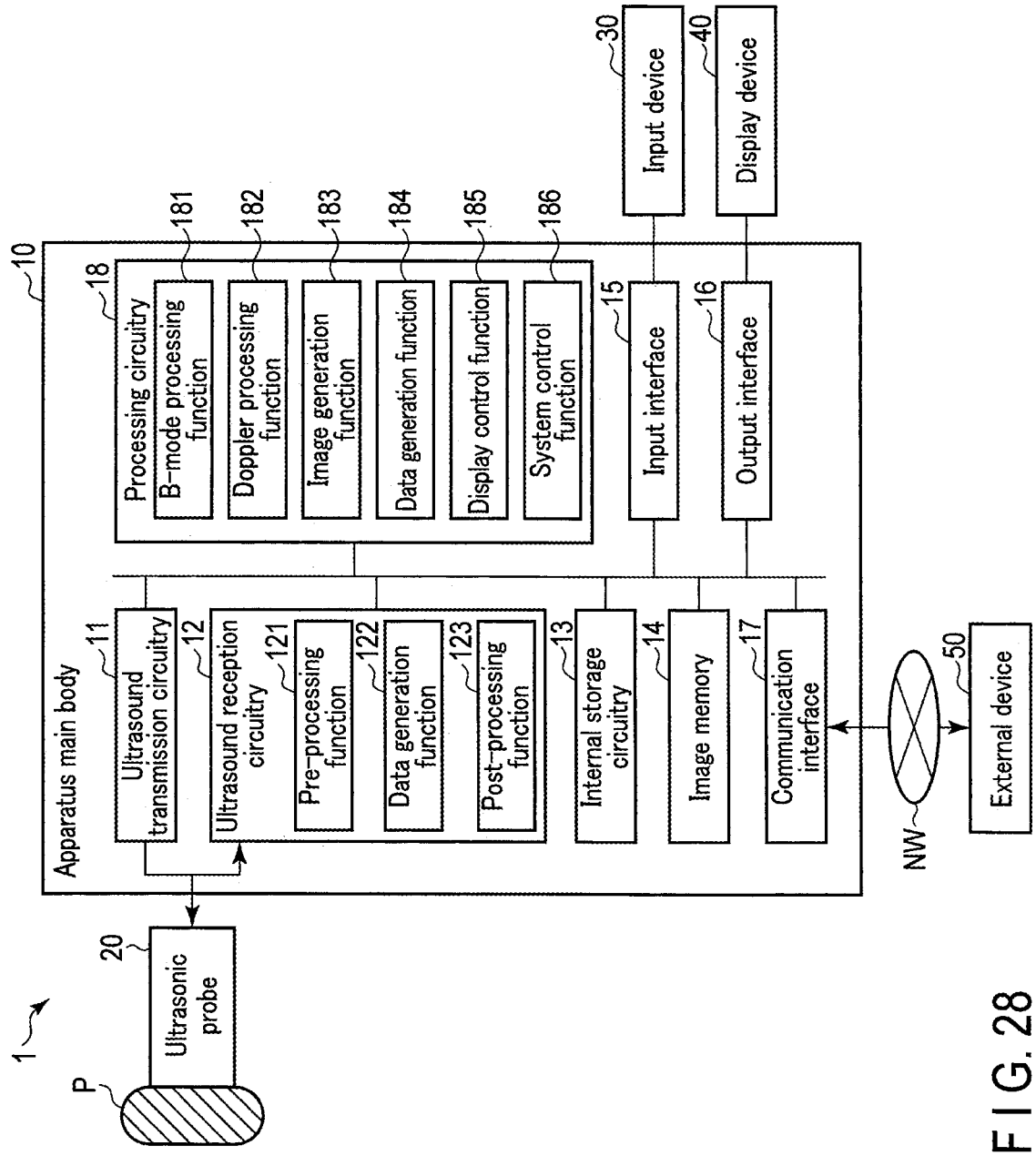
FIG. 28 is a block diagram showing an exemplary structure of an ultrasonic diagnostic apparatus according to the third embodiment.

FIG. 28 is a block diagram illustrating an exemplary configuration of an ultrasonic diagnostic apparatus 1 according to the third embodiment. In the third embodiment, both the ultrasound reception circuitry 12 and processing circuitry 18 are provided with a data generation function. This means that, in the third embodiment, the data generation function 184 of the processing circuitry 18 in the first embodiment and the data generation function 122 of the ultrasound reception circuitry 12 in the second embodiment are combined.

As described in the first embodiment, when the input data and supervisory data are combined, two types of combinations are possible; a combination through the PM as illustrated in FIG. 9 and a combination through the AM as illustrated in FIG. 10. In addition, the data generation function 184 can be implemented at any of the four points as explained in the first embodiment, and the data generation function 122 can be implemented at either one of the two points as explained in the second embodiment. In addition to these combinations, two or more data generation functions 122 and 184 may also be adopted.

The ultrasonic diagnostic apparatus 1 may implement both of the data generation function 122 of the ultrasound reception circuitry 12 in FIG. 22 and the data generation function 184 of the processing circuitry 18 in FIG. 13. After implementing the upstream data generation function 122, the downstream data generation function 184 is implemented. In this case, with the data generation function 122, the ultrasound reception circuitry 12 that serves as a generation processing section enters input data based on the matrix data processed with the pre-processing function 121 to a trained model for generating output data based on the matrix data derived from a non-linear signal, using input data based on the matrix data derived from a fundamental wave signal, as a result of which output data is generated based on the matrix data derived from the non-linear signal. Furthermore, with the data generation function 184, the processing circuitry 18 that serves as a generation section generates output data based on ultrasonic image data derived from a non-linear signal, using input data based on ultrasonic image data derived from a fundamental wave signal. Alternatively, the ultrasonic diagnostic apparatus 1 may implement both of the data generation function 122 of the ultrasound reception circuitry 12 in FIG. 27 and the data generation function 184 of the processing circuitry 18 in FIG. 13. The ultrasound reception circuitry 12 may implement two or more data generation functions 122, or the processing circuitry 18 may implement two or more data generation functions 184.

According to the present embodiment, two data generation functions 122 and 184 are used in combination, thereby enhancing the quality of the generated ultrasonic images.

Fourth Embodiment

In the above embodiments, the apparatus main body 10 including the ultrasound transmission circuitry 11 and ultrasound reception circuitry 12 has been described. In the fourth embodiment, an ultrasonic probe 20a including the ultrasound transmission circuitry 11 and ultrasound reception circuitry 12 will be described.

Figure 29:
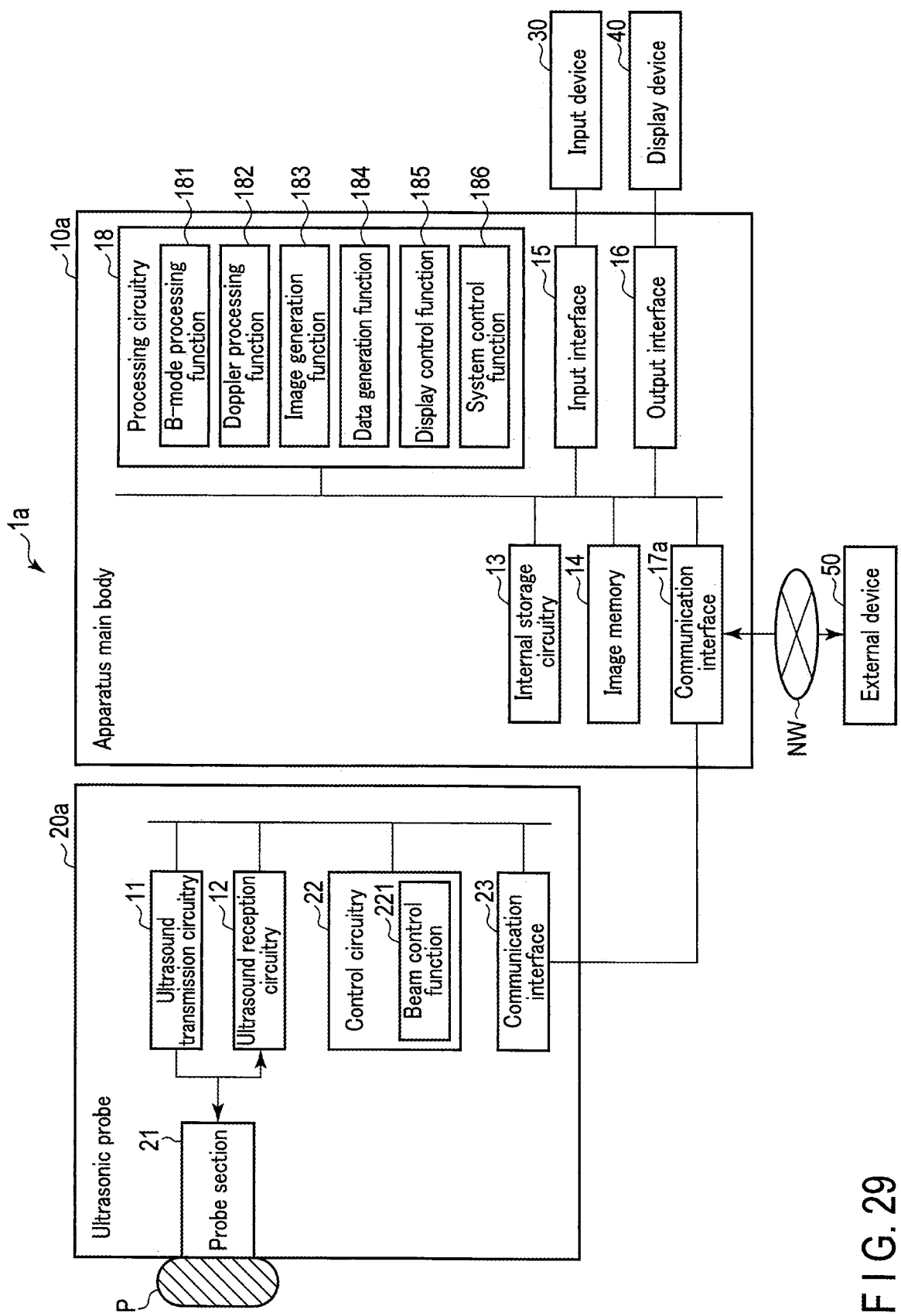
FIG. 29 is a block diagram showing an exemplary structure of an ultrasonic diagnostic apparatus according to the fourth embodiment.

FIG. 29 is a block diagram showing an exemplary structure of the ultrasonic diagnostic apparatus according to the fourth embodiment. As illustrated in FIG. 27, an ultrasonic diagnostic apparatus 1a includes an apparatus main body 10a and an ultrasonic probe 20a. The apparatus main body 10a is connected to the input device 30 and display device 40. The apparatus main body 10a is also connected to the external device 50 by way of a network NW. The ultrasonic probe 20a is detachably coupled to the apparatus main body 10a.

The ultrasonic probe 20a includes a probe section 21, ultrasound transmission circuitry 11, ultrasound reception circuitry 12, control circuitry 22 and a communication interface 23. The ultrasonic probe 20a may be provided with a button or the like that is pressed when performing offset processing or freezing of an ultrasonic image, as an input interface.

The probe section 21 includes, for example, a plurality of piezoelectric vibrators, matching layers provided on the respective piezoelectric vibrators, and a backing member for preventing backward propagation of ultrasonic waves from the piezoelectric vibrators. The probe section 21 generates ultrasonic waves by the piezoelectric vibrators, based on a drive signal supplied from the ultrasound transmission circuitry 11. When an ultrasonic wave is transmitted from the probe section 21 to the subject P, the transmitted ultrasonic wave is sequentially reflected on the acoustic impedance discontinuous surface of the body tissue of the subject P. The probe section 21 receives the reflected wave by the piezoelectric vibrators. The probe section 21 converts the received reflected wave into a reflection wave signal.

The control circuitry 22 is, for example, a processor that controls operations relating to ultrasound scanning. The control circuitry 22 implements an operation program stored in the internal storage circuitry 13 of the apparatus main body 10a, thereby realizing functions corresponding to this operation program. Specifically, the control circuitry 22 includes a beam control function 221.

The beam control function 221 is not limited to an operation program stored and incorporated in the internal storage circuitry 13. The beam control function 221 may be incorporated in the control circuitry 22. Furthermore, the beam control function 221 may be integrated into the system control function 186 of the processing circuitry 18 in the apparatus main body 10a.

With the beam control function 221, the control circuitry 22 sets control parameters for the ultrasound transmission circuitry 11 and ultrasound reception circuitry 12. In particular, the control circuitry 22 reads information such as a transmission position, transmission openings, and transmission delay from a memory (not shown), and sets the read-out information into the ultrasound transmission circuitry 11. Similarly, the control circuitry 22 sets the read-out information into the ultrasound reception circuitry 12.

The control circuitry 22 controls the ultrasound transmission circuitry 11 and the ultrasound reception circuitry 12 based on the control parameters that have been set, and performs ultrasound scanning corresponding to a respective one of various imaging modes.

The communication interface 23 is connected to the apparatus main body 10a in a wired or wireless manner, and performs data communications with the apparatus main body 10a. In particular, the communication interface 23 receives instructions from the system control function 186 of the processing circuitry 18 in the apparatus main body 10a, and outputs the received instructions to the control circuitry 22. Furthermore, the communication interface 23 outputs the reception signal generated by the ultrasound reception circuitry 12 to the processing circuitry 18. The above-mentioned wired manner may be realized by a universal serial bus (USB), but is not limited thereto.

The apparatus main body 10a illustrated in FIG. 27 is an apparatus for generating an ultrasonic image based on a reception signal output by the ultrasonic probe 20a. The apparatus main body 10a includes internal storage circuitry 13, an image memory 14, an input interface 15, an output interface 16, a communication interface 17a, and processing circuitry 18.

The communication interface 17a is connected to the ultrasonic probe 20a in a wired or wireless manner, and performs data communications with the ultrasonic probe 20a. In particular, the communication interface 17a outputs the instructions from the system control function 186 of the processing circuitry 18 to the ultrasonic probe 20a. The communication interface 17a further outputs a reception signal generated by the ultrasonic probe 20a to the apparatus main body 10a. The communication interface 17a may be connected to an external device 50 via a network NW, and perform data communications with the external device 50.

The configurations of the ultrasonic probe 20a and apparatus main body 10a are not limited to the above. The ultrasonic probe 20a may include a memory for storing a control program for realizing ultrasound transmission/reception. Furthermore, the ultrasound reception circuitry 12 may be provided with a pre-processing function 121, data generation function 122 and post-processing function 123.

At least one of the components of the apparatus main body 10a according the present embodiment may be included in the ultrasonic probe 20a. In this case, the ultrasonic probe 20a may be connected to a display device 40 (e.g., display, tablet terminal and smart phone) for displaying ultrasonic images, via USB or in a wireless manner.

The apparatus main body 10a may include the input device 30 and display device 40. If this is the case, the apparatus main body 10a may be realized by a terminal device such as a tablet terminal or smart phone.

Fifth Embodiment

In the fifth embodiment, a trained model will be explained, which generates output data based on a combined signal of a plurality of ultrasonic signals, using input data based on an ultrasonic signal. In the explanation below, as input data and output data (or supervisory data), the data acquired after beam forming is mainly used.

The structure of the ultrasonic diagnostic apparatus according to the fifth embodiment is approximately the same as the structure of the ultrasonic diagnostic apparatus according to the first embodiment. The ultrasonic diagnostic apparatus according to the fifth embodiment is therefore explained by referring to FIG. 1. The explanation of the same components is omitted.

In the ultrasonic diagnostic apparatus according to the fifth embodiment, the data generation function 184 is configured to generate output data based on a combined signal, by inputting an ultrasonic signal acquired through an examination, to a trained model for using input data based on an ultrasonic signal and thereby generating output data based on a combined signal acquired by combining multiple ultrasonic signals. With the data generation function 184, the processing circuitry 18 may use, as input data, ultrasonic image data generated with the image generation function 183. A trained model may generate, using input data based on an ultrasonic signal received at a scan position, output data based on a combined signal of ultrasonic signals received at the scan position. The data generation function 184 will be described in detail later.

Figure 30:
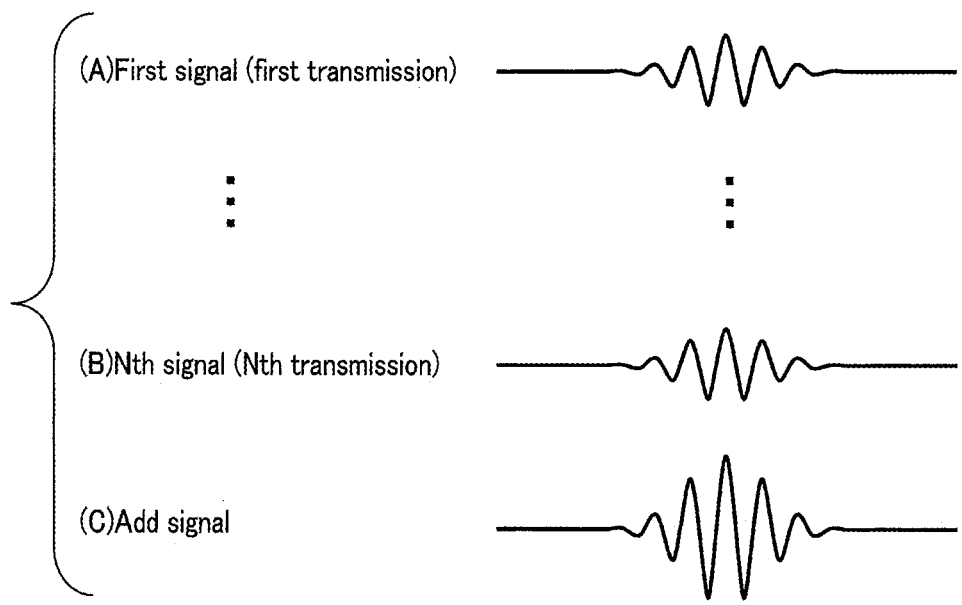
FIG. 30 is a diagram showing examples of transmission waveforms of multiple ultrasonic waves and a composite waveform obtained by combining the transmission waveforms according to the fifth embodiment.

FIG. 30 is a diagram showing examples of transmission waveforms of multiple ultrasonic waves and a composite waveform acquired by combining the transmission waveforms. In the ultrasonic diagnostic apparatus 1, the ultrasound transmission circuitry 11 may conduct the ultrasound transmission of the same acoustic pressure (amplitude) multiple times. The ultrasound transmission circuitry 11 may conduct the ultrasound transmission on the same scan position N times, using at least an ultrasonic wave that is the first signal indicated as (A) in FIG. 30 and an ultrasonic wave that is the N-th signal indicated as (B) in FIG. 30. In the explanation below, it is assumed that N=2, which is not a limitation. The amplitude (acoustic pressure) of the first signal is approximately the same as the amplitude of the second signal. The ultrasound reception circuitry 12 generates a first reception signal from the ultrasound transmission of the first signal and a second reception signal from the ultrasound transmission of the second signal. The waveforms of the first signal and the second signal indicated in FIG. 30 are approximately the same as the waveforms of the respective reception signals (reception waveforms). Thus, FIG. 30 may be referred to when explaining the waveforms, for both transmission and reception waveforms.

With the B-mode processing function 181, the processing circuitry 18 generates an add signal (combined signal) that indicates the sum of the first signal and the second signal. FIG. 30 shows a combined waveform as (C), which is an add signal. The combined waveform of (C) in FIG. 30 is subjected to the addition processing, and thus has a greater amplitude and greater signal-to-noise ratio than the waveforms of (A) and (B) in FIG. 30.

In other words, the processing circuitry 18 is configured to combine the first signal with the second signal to generate a combined signal. That is, a combined signal is a signal acquired by combining multiple ultrasonic signals.

Figure 31:
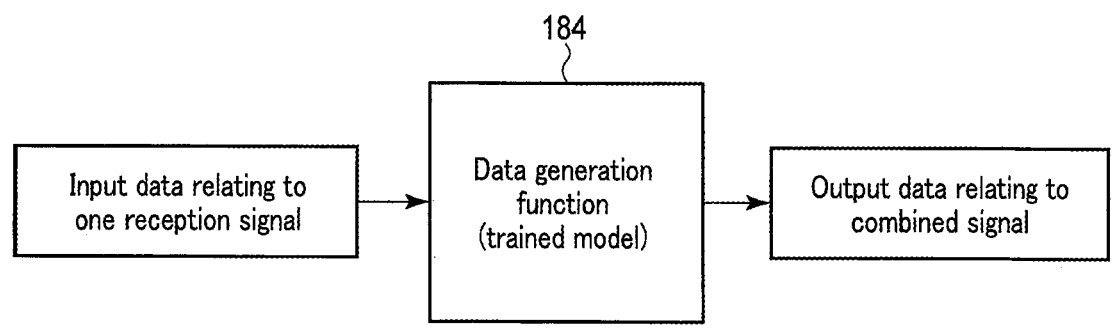
FIG. 31 is a diagram explaining a concept of data input to and output from the data generation function of the processing circuitry according to the fifth embodiment.

FIG. 31 is a diagram explaining the concept of data input to and output from the data generation function 184 of the processing circuitry 18 in the ultrasonic diagnostic apparatus 1 according to the present embodiment. In the ultrasonic diagnostic apparatus 1, input data based on one reception signal (ultrasonic signal) received by the ultrasound reception circuitry 12 in relation to one ultrasound transmission from the ultrasound transmission circuitry 11 is input to the data generation function 184 of the processing circuitry 18. The input data may be a first signal in an ultrasound transmission as indicated as (A) in FIG. 30. That is, the input data is an ultrasonic signal acquired through a single ultrasound transmission. The processing circuitry 18 generates output data based on a combined signal by applying the input data based on the ultrasonic signal to a trained model for generating output data based on a combined signal acquired by combining a plurality of ultrasonic signals. The output data based on the combined signal is output from the data generation function 184 of the processing circuitry 18. Training with the data generation function will be described later in detail. The input data may be the second signal acquired through the ultrasound transmission as illustrated as (B) in FIG. 30.

Figure 32:
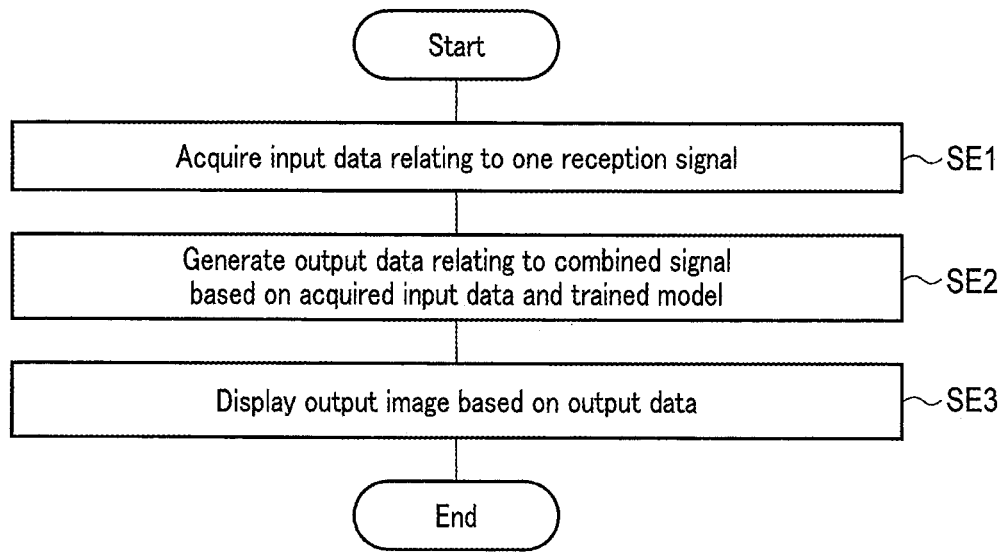
FIG. 32 is a flowchart of an exemplary operation of the processing circuitry with the data generation function according to the fifth embodiment.

FIG. 32 is a flowchart of an exemplary operation of the processing circuitry 18 with the data generation function 184. At step SE1, the processing circuitry 18 acquires input data relating to one reception signal. At step SE2, the processing circuitry 18 generates output data relating to a combined signal, based on the acquired input data and trained model. At step SE3, the processing circuitry 18 displays an output image on the display device 40 based on the output data.

As explained above, in the ultrasonic diagnostic apparatus 1 according to the fifth embodiment, the processing circuitry 18 generates output data based on a combined signal, by inputting input data based on an ultrasonic signal acquired through an examination into a trained model for generating output data based on a combined signal acquired by combining a plurality of ultrasonic signals, using input data based on an ultrasonic signal. In this manner, data generation can be achieved. That is, even if a signal (ultrasonic signal) is acquired from a reception beam of a single reception, an ultrasonic image of an image quality as high as that of an ultrasonic image generated from a combined signal can be obtained.

The combined signal used in the fifth embodiment may be a non-linear signal. For example, if the ultrasonic signals are non-linear signals, the combined signal also becomes a non-linear signal. Thus, the ultrasonic diagnostic apparatus 1 according to the fifth embodiment can generate ultrasonic image data of a high image quality relating to a non-linear signal through ultrasound transmissions, the number of which is reduced in comparison to the conventional technique.

(Examples of Trained Model Generation)

The trained model according to the fifth embodiment has a function of outputting an ultrasonic image based on a combined signal acquired by combining a plurality of ultrasonic signals, using the input of an ultrasonic image based on an ultrasonic signal. In this case, the training data includes input data that is an ultrasonic image based on the ultrasonic signal, and supervisory data that is an ultrasonic image based on a combined signal.

Figure 33:
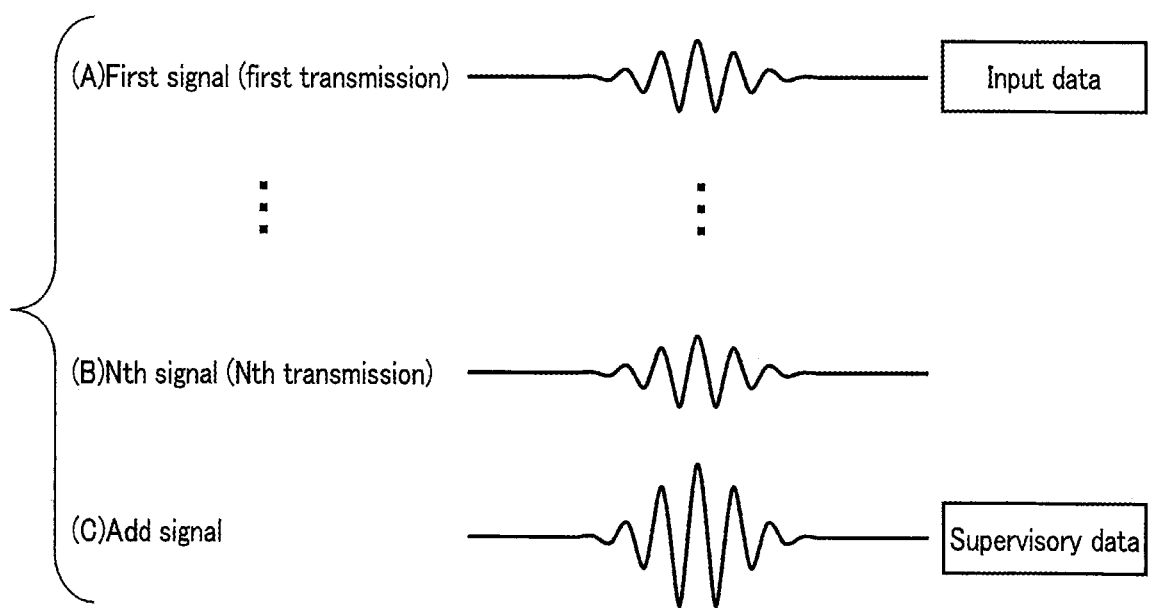
FIG. 33 is a diagram showing exemplary transmission waveforms of ultrasonic waves for generation and use of a trained model according to the fifth embodiment.

The input data and supervisory data used by the learning apparatus 60 for machine learning will be explained below with reference to FIG. 33. Exemplary transmission waveforms of ultrasound waves for generation and use of a trained model are illustrated in FIG. 33. The waveforms corresponding to the signals in FIG. 33 are the same as those in FIG. 30.

For example, as illustrated as (A) in FIG. 33, the learning apparatus 60 may adopt the first reception signal acquired through the ultrasound transmission of the first signal, as input data for training. Moreover, as illustrated as (C) in FIG. 33, the learning apparatus 60 adopts an add signal acquired from the sum of the first reception signal through the ultrasound transmission of the first signal and the second reception signal through the ultrasound transmission of the second signal, as supervisory data. Here, the first reception signal and second reception signal are acquired from the same scan position. The second reception signal may be used as input data for training.

As explained by referring to FIG. 33, the input data that is input to the trained model (data generation function 184) at the time of using the ultrasonic diagnostic apparatus 1 is a first reception signal through the ultrasound transmission of a first signal, as illustrated in (A) of FIG. 30. That is, the input data at the usage is an ultrasonic signal acquired through a single ultrasound transmission.

FIG. 11 is a diagram showing a specific example of generation of a trained model generated by the learning apparatus 60. In the learning apparatus 60, input data that is, for example, ultrasonic image data generated based on an ultrasonic signal as indicated in (A) of FIG. 33 is input into the machine learning model 61 (CNN). The learning apparatus 60 applies the CNN to the input data relating to an ultrasonic signal, and thereby generates output data relating to a combined signal acquired by combining a plurality of ultrasonic signals, as shown in FIG. 5. The output data relating to the combined signal is output from the CNN. In the learning apparatus 60, the output data is entered into the evaluation function 62. Furthermore, in the learning apparatus 60, supervisory data that is, for example, ultrasonic image data generated based on the combined signal in (C) of FIG. 33 is entered into the evaluation function 62. The learning apparatus 60 evaluates, with the evaluation function 62, the output data generated by the machine learning model (CNN) based on the input data, and the supervisory data. The evaluation function 62 may compare the generated output data with the supervisory data, and correct the coefficients of the CNN (network parameters such as weight and bias) through backpropagation. In this manner the evaluation obtained with the evaluation function 62 is fed back to the CNN. The learning apparatus 60 repeats a series of supervised learning operations based on the training data that is a set of input data and supervisory data acquired with respect to the same position of the subject until, for example, the error between the output data and the supervisory data becomes smaller than or equal to a predetermined threshold value. The learning apparatus 60 may output the trained machine learning model as a trained model.

In the above explanation, it is assumed that the learning apparatus 60 generates a trained model before the factory shipment so that the model can be used by the ultrasonic diagnostic apparatus 1 at the time of an ultrasonic examination. The usage mode, however, is not limited thereto. At usual ultrasonic examinations conducted by the ultrasonic diagnostic apparatus 1 equipped with the learning apparatus 60, the learning apparatus 60 (ultrasonic diagnostic apparatus 1) may perform real-time training. If this is the case, the ultrasonic diagnostic apparatus 1 acquires a combined signal through a plurality of ultrasound transmissions, as indicated in (C) of FIG. 33. The input data here represents ultrasonic signals acquired through respective ultrasound transmissions. The ultrasonic diagnostic apparatus 1 generates input data (ultrasonic signal in (A) of FIG. 33) that serves as training data and supervisory data (combined signal in (C) of FIG. 33), and thereby performs training with the training data. In this manner, the existing trained model can be updated even after the factory shipment.

As explained above, the learning apparatus 60 (CNN, data generation function) according to the present embodiment generates a trained model for generating output data based on a combined signal by using input data based on an ultrasonic signal, wherein the learning apparatus 60 acquires input data based on an ultrasonic signal and supervisory data based on the combined signal acquired by combining multiple ultrasonic signals through at least two ultrasound transmissions, and performs machine learning on the machine learning model based on the input data and supervisory data. The at least two ultrasound transmissions are implemented by using ultrasonic waves having the same acoustic pressure with respect to the same scan direction (see, for example, FIG. 33).

Next, as the input data and output data (or supervisory data) according to the fifth embodiment, the use of data before being subjected to beam forming is explained.

Figure 34:
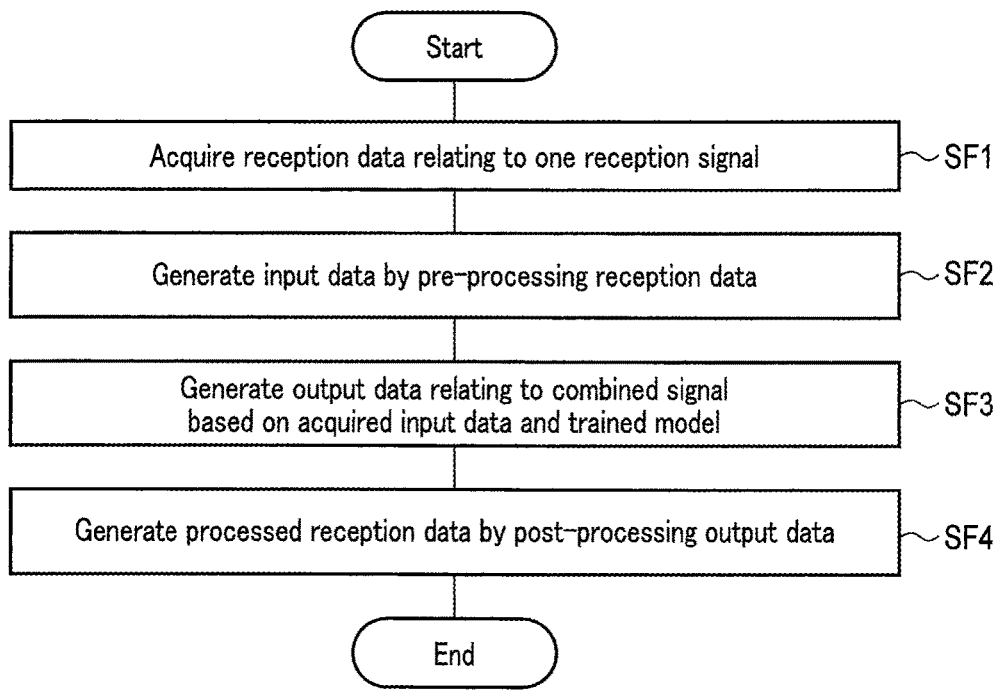
FIG. 34 is a flowchart of an exemplary operation of the ultrasound reception circuitry with the data generation function according to the fifth embodiment.

FIG. 34 is a flowchart of an exemplary operation of the ultrasound reception circuitry 12 with the data generation function 122. At step SF1, the ultrasound reception circuitry 12 acquires reception data relating to one reception signal. At step SF2, the ultrasound reception circuitry 12 implements the pre-processing on the reception data to generate input data. At step SF3, the ultrasound reception circuitry 12 generates output data relating to a combined signal, based on the generated input data and trained model. At step SF4, the ultrasound reception circuitry 12 implements the post-processing based on the output data to generate processed reception data.

In the ultrasonic diagnostic apparatus according to the first to fifth embodiments overall, the processing circuitry acquires output data from a trained model by entering examination data acquired at an examination, the examination data corresponding to first data, the output data corresponding to second data, into the trained model configured to, based on the first data acquired through transmission of an ultrasound wave for a first number of times, output the second data acquired through transmission of an ultrasound wave for a second number of times that is greater than the first number of times.

The first data may be data based on the fundamental wave signal of an ultrasonic wave, and the second data may be data based on the non-linear signal of an ultrasonic wave. Alternatively, the second data may be data acquired by combining a plurality of data items that are acquired through transmission of an ultrasound wave for the second number of times. The first data may be any of (a) data that has not yet been subjected to beam forming, (b) data subjected to beam forming but prior to being subjected to envelope detection processing, (c) data subjected to envelope detection processing but prior to being subjected to logarithmic compression, and (d) data subjected to logarithmic compression processing but prior to being subjected to scan conversion. The trained model may be a convolution neural network. The first number of times may be 1.

If the first data has not yet been subjected to beam forming, the ultrasonic diagnostic apparatus performs the beam forming based on the second data output by the trained model.

If the first data has been subjected to beam forming but is prior to being subjected to envelope detection processing, the ultrasonic diagnostic apparatus performs the envelope detection processing based on the second data output by the trained model.

If the first data has been subjected to envelope detection processing but is prior to being subjected to logarithmic compression processing, the ultrasonic diagnostic apparatus performs the logarithmic compression processing based on the second data output by the trained model.

If the first data has been subjected to data logarithmic compression processing but is prior to being subjected to scan conversion, the ultrasonic diagnostic apparatus performs the scan conversion based on the second data output by the trained model.

The apparatus that implements the above operations is not limited to an ultrasonic diagnostic apparatus. A computer (processing device) such as a workstation may perform the above operations.

Sixth Embodiment

In the sixth embodiment, a trained model will be explained which generates output data based on a high acoustic pressure signal of an ultrasonic wave, using input data based on a low acoustic pressure signal of an ultrasonic wave. In the explanation below, the use of data subjected to beam forming will mainly be discussed as input data and output data (or supervisory data).

The structure of the ultrasonic diagnostic apparatus according to the sixth embodiment is approximately the same as the structure of the ultrasonic diagnostic apparatus according to the first embodiment. The ultrasonic diagnostic apparatus according to the sixth embodiment therefore will be explained by referring to FIG. 1, and the explanation of the same components is omitted.

In the ultrasonic diagnostic apparatus according to the sixth embodiment, the data generation function 184 is configured to generate output data based on a high acoustic pressure signal of an ultrasonic wave by inputting input data based on a low acoustic pressure signal of an ultrasonic wave acquired through an examination, to a trained model for generating output data based on a high acoustic pressure signal of an ultrasonic wave by using input data based on the low acoustic pressure signal. With the data generation function 184, the processing circuitry 18 may use, as input data, ultrasonic image data generated with the image generation function 183. The trained model may generate, using input data based on a low acoustic pressure signal received at a scan position, output data based on a high acoustic pressure signal received at the scan position. The data generation function 184 will be described in detail later.

Figure 35:
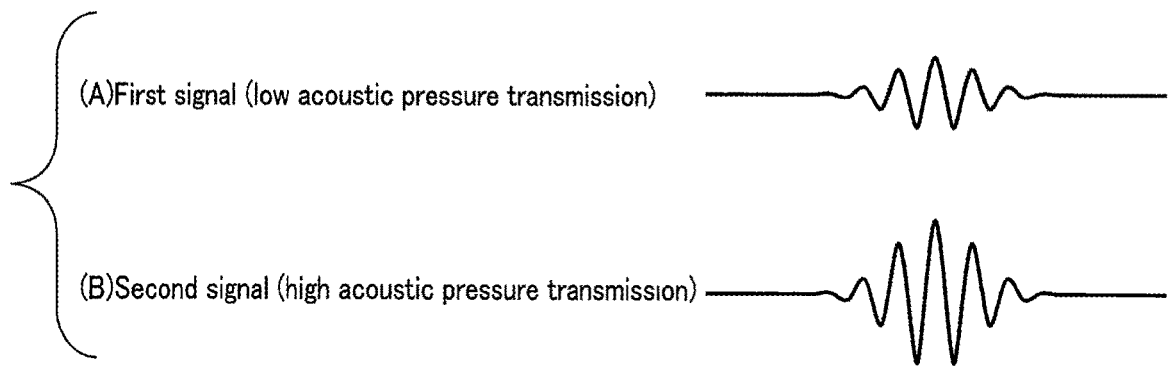
FIG. 35 is a diagram showing exemplary transmission waveforms of ultrasonic waves having different acoustic pressures according to the sixth embodiment.

FIG. 35 is a diagram showing exemplary transmission waveforms of ultrasonic waves having different acoustic pressures. In the ultrasonic diagnostic apparatus 1, the ultrasound transmission circuitry 11 may conduct ultrasound transmissions of different acoustic pressures (amplitudes). The ultrasound transmission circuitry 11 may implement to the same scan position a low acoustic pressure transmission using a first signal as indicated in (A) of FIG. 35, and a high acoustic pressure transmission using a second signal in (B) of FIG. 35. The amplitude (acoustic pressure) of the first signal is smaller than the amplitude of the second signal. The ultrasound reception circuitry 12 generates a reception signal relating to the low acoustic pressure transmission, and a reception signal relating to a high acoustic pressure transmission. The waveforms of the first signal and the waveform of the second signal in FIG. 35 are approximately the same as the waveforms of their respective reception signals (reception waveforms). Thus, in the following explanation of waveforms, FIG. 35 may be referred to, regardless of the waveform relating to transmission or to reception. The first signal and second signal may be referred to as a low acoustic pressure signal and high acoustic pressure signal.

FIG. 36 is a diagram explaining the concept of data input to and output from the data generation function 184 of the processing circuitry 18 in the ultrasonic diagnostic apparatus 1 according to the present embodiment. In the ultrasonic diagnostic apparatus 1, input data based on a low acoustic pressure signal received by the ultrasound reception circuitry 12 in a low acoustic pressure transmission of the ultrasound transmission circuitry 11 is input to the data generation function 184 of the processing circuitry 18. The input data may be a first signal by the low acoustic pressure transmission indicated as (A) in FIG. 35. That is, the input data is a reception signal with a small amplitude. The processing circuitry 18 generates output data based on a high acoustic pressure signal of an ultrasonic wave by applying a trained model for generating output data based on a high acoustic pressure signal to the input data relating to a low acoustic pressure transmission. The output data based on the high acoustic pressure signal is output from the data generation function 184 of the processing circuitry 18. Training with the data generation function will be described later in detail.

FIG. 37 is a flowchart of an exemplary operation of the processing circuitry 18 with the data generation function 184. At step SG1, the processing circuitry 18 acquires input data relating to the low acoustic pressure transmission. At step SG2, the processing circuitry 18 generates output data relating to the high acoustic pressure transmission, based on the acquired input data and trained model. At step SG3, the processing circuitry 18 displays an output image on the display device 40, based on the output data.

As explained above, in the ultrasonic diagnostic apparatus 1 according to the sixth embodiment, the processing circuitry 18 generates output data based on the high acoustic pressure signal by entering input data based on a low acoustic pressure signal of an ultrasonic wave acquired through an examination to a trained model for generating output data based on a high acoustic pressure signal of an ultrasonic wave by using input data based on the low acoustic pressure signal of an ultrasonic wave. In this manner, regardless of the level of the acoustic pressure, ultrasonic diagnostic image data with a high signal-to-noise ratio can be generated. That is, even if the signal is acquired from a reception beam with a small acoustic pressure (i.e., low acoustic pressure signal), a high-quality ultrasonic image similar to an ultrasonic image generated from a high acoustic pressure signal can be acquired.

The low acoustic pressure signal and high acoustic pressure signal used in the sixth embodiment may be non-linear signals. For example, if the low acoustic pressure signal and high acoustic pressure signal are fundamental wave signals, a difference between their acoustic pressures corresponds to a difference between the signal-to-noise ratios. If non-linear signals are used, the difference between the low acoustic pressure signal and the high acoustic pressure signal corresponds to a difference in the signal-to-noise ratios and to a difference in nonlinearity. In THI, for example, the bearing resolution, which is proportional to the square of the acoustic pressure, is enhanced with a higher acoustic pressure, or in other words, with the use of a high acoustic pressure signal. Through the use of non-linear signals for a low acoustic pressure signal and high acoustic pressure signal, the ultrasonic diagnostic apparatus 1 according to the sixth embodiment can generate ultrasonic image data of a high signal-to-noise ratio and excellent bearing resolution, regardless of the level of the acoustic pressure.

(Examples of Trained Model Generation)

The trained model according to the sixth embodiment has a function of outputting an ultrasonic image based on a high acoustic pressure signal, using the input of an ultrasonic image based on a low acoustic pressure signal. Here, the training data includes input data that is an ultrasonic image based on a low acoustic pressure signal, and supervisory data that is an ultrasonic image based on a high acoustic pressure signal.

The input data and supervisory data used by the learning apparatus 60 for machine learning will be explained below with reference to FIG. 38. Exemplary transmission waveforms of ultrasound waves for generation and use of a trained model are illustrated in FIG. 38. The waveforms corresponding to the signals illustrated in FIG. 38 are the same as in FIG. 35.

The learning apparatus 60 may adopt the first reception signal acquired through the ultrasound transmission of the first signal illustrated as (A) in FIG. 38, as input data for training. Moreover, the learning apparatus 60 adopts a second reception signal acquired through the ultrasound transmission of a second signal illustrated as (B) in FIG. 38, as supervisory data. Here, the first reception signal and second reception signal are acquired from the same scan position.

As explained with reference to FIG. 38, the input data that is input to the trained model (data generation function 184) at the use of the ultrasonic diagnostic apparatus 1 is a first reception signal through the ultrasound transmission of a first signal, as illustrated in (A) of FIG. 35. That is, the input data at this use is a low acoustic pressure signal acquired through a single ultrasound transmission.

A signal with both the amplitude and phase of a transmission ultrasonic wave being changed may be adopted; however, the explanation of such use is omitted here.

FIG. 11 is a diagram showing a specific example of the generation of a trained model generated by the learning apparatus 60. In the learning apparatus 60, the input data that is, for example, the ultrasonic image data generated based on a low acoustic pressure signal as in (A) of FIG. 38 is input to the machine learning model 61 (CNN). The learning apparatus 60 applies the CNN to the input data relating to a low acoustic pressure signal, and thereby generates output data relating to a high acoustic pressure signal, as shown in FIG. 5. The output data relating to the high acoustic pressure signal is output from the CNN. In the learning apparatus 60, the output data is entered into the evaluation function 62. Furthermore, in the learning apparatus 60, supervisory data that is, for example, ultrasonic image data generated based on a high acoustic pressure signal as in (B) of FIG. 38 is entered into the evaluation function 62. The learning apparatus 60 evaluates, with the evaluation function 62, the output data generated by the machine learning model (CNN) based on the input data, and the supervisory data. The evaluation function 62 may compare the generated output data with the supervisory data and correct the coefficients of the CNN (network parameters such as weight and bias) through backpropagation. In this manner, the evaluation with the evaluation function 62 is fed back to the CNN. The learning apparatus 60 repeats a series of supervised learning operations based on the training data that includes a set of input data and supervisory data acquired with respect to the same position of the subject, for example, until the error between the output data and the supervisory data becomes smaller than or equal to a predetermined threshold value. The learning apparatus 60 may output the trained machine learning model as a trained model.

In the above explanation, it is assumed that the learning apparatus 60 generates a trained model before the factory shipment so that the model can be used by the ultrasonic diagnostic apparatus 1 at the time of an ultrasonic examination. The usage mode, however, is not limited thereto. At usual ultrasonic examinations conducted by the ultrasonic diagnostic apparatus 1 equipped with the learning apparatus 60, the learning apparatus 60 (ultrasonic diagnostic apparatus 1) may perform real-time training. If this is the case, after acquiring a first reception signal through a low acoustic pressure transmission based on the first signal as indicated in (A) of FIG. 38, upon the operator switching the ultrasonic output, the ultrasonic diagnostic apparatus 1 acquires a second reception signal based on the second signal as indicated in (B) of FIG. 38. The ultrasonic diagnostic apparatus 1 generates input data (a low acoustic pressure signal in (A) of FIG. 38) that serves as training data and supervisory data (a high acoustic pressure signal in (B) of FIG. 38), and thereby performs training with the training data. In this manner, the existing trained model can be updated even after the factory shipment.

As described above, according to the present embodiment, the learning apparatus 60 (CNN, data generation function) generates a trained model through machine learning using input data based on a low acoustic pressure signal and supervisory data based on a high acoustic pressure signal. The ultrasonic diagnostic apparatus 1 equipped with this trained model outputs an ultrasonic image based on a high acoustic pressure signal through inference from the reception signal relating to the transmission of a low acoustic pressure signal of an ultrasonic wave, using the result of the machine learning.

Next, as the input data and output data (or supervisory data) according to the sixth embodiment, the use of data that has not yet been subjected to beam forming is explained.

FIG. 39 is a flowchart of an exemplary operation of the ultrasound reception circuitry 12 with the data generation function 122. At step SH1, the ultrasound reception circuitry 12 acquires reception data relating to a low acoustic pressure transmission. At step SH2, the ultrasound reception circuitry 12 implements the pre-processing on the reception data to generate input data. At step SH3, the ultrasound reception circuitry 12 generates output data relating to the high acoustic pressure transmission, based on the generated input data and trained model. At step SH4, the ultrasound reception circuitry 12 implements the post-processing on the output data to generate processed reception data.

In the ultrasonic diagnostic apparatus of these embodiments according to the first to sixth embodiments overall, the processing circuitry acquires second data from the trained model by inputting examination data acquired at an examination, which corresponds to the first data, to a trained model for outputting second data that differs from the first data acquired through the transmission of an ultrasonic wave, using the first data acquired through the transmission of an ultrasonic wave. The first input data is any of (a) data that has not yet been subjected to beam forming, (b) data subjected to beam forming but prior to being subjected to envelope detection processing, (c) data subjected to envelope detection processing but prior to being subjected to logarithmic compression, and (d) data subjected to logarithmic compression processing but prior to being subjected to scan conversion. The trained model may be a convolution neural network.

If the first data has not yet been subjected to beam forming, the ultrasonic diagnostic apparatus performs the beam forming based on the second data output by the trained model.

If the first data is data subjected to beam forming but prior to being subjected to envelope detection processing, the ultrasonic diagnostic apparatus performs the envelope detection processing based on the second data output by the trained model.

If the first data is data subjected to the envelope detection processing but prior to being subjected to logarithmic compression processing, the ultrasonic diagnostic apparatus performs the logarithmic compression processing based on the second data output by the trained model.

If the first input data is data subjected to the logarithmic compression processing but prior to being subjected to scan conversion, the ultrasonic diagnostic apparatus performs the scan conversion, based on the second data output by the trained model.

The apparatus that implements the above operations is not limited to an ultrasonic diagnostic apparatus. A computer (processing device) such as a workstation may perform the above operations.

Other Embodiments

The functions according to the above embodiments may also be implemented by installing programs that implement respective processes in a computer, such as a workstation, and loading them in the memory. A program for having the computer implement the method may be stored and distributed in storage media such as a magnetic disk (e.g. a hard disk), an optical disk (e.g. a CD-ROM or a DVD), and a semiconductor memory.

According to at least one embodiment described above, an ultrasonic image of a high quality can be acquired through fewer ultrasound transmissions than in the conventional technique.

The above term "processor" may represent any circuit such as a central processing unit (CPU) or graphics processing unit (GPU), or may be an application specific integrated circuit (ASIC), programmable logic device (e.g., simple programmable logic device (SPLD), complex programmable logic device (CPLD), and field programmable gate array (FPGA)). The processor realizes the functions by reading and executing the program stored in the memory circuitry. Each of the processors according to the embodiments of the present invention are not limited to a respective circuit for each processor, but may be configured as one processor by combining independent circuits to realize the functions. Furthermore, a plurality of structural elements in FIGS. 1, 18, 28 and 29 may be integrated into one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A processing apparatus comprising processing circuitry configured to:
   acquire first subject data including a fundamental wave signal and a harmonic signal of an ultrasound wave;
   input the acquired first subject data into a trained model; and
   acquire second subject data output from the trained model, the second subject data corresponding to data in which an amplitude of the fundamental wave signal of the ultrasound wave included in the first subject data is reduced and which is based on an amplitude of a harmonic signal of the ultrasound wave included in the first subject data which is increased,
   wherein the trained model is a model that has been trained, based on input of first ultrasound wave data, to output second ultrasound wave data corresponding to data in which an amplitude of a fundamental wave signal included in the first ultrasound wave data is reduced, and which is based on an amplitude of a harmonic signal included in the first ultrasound wave data which is increased.

2. The processing apparatus according to claim 1, wherein the second subject data corresponds to data generated by combining a plurality of data items acquired through at least two transmissions of the ultrasound wave.

3. The processing apparatus according to claim 1, wherein the first subject data corresponds to any one of:
   (a) data prior to being subjected to beam forming;
   (b) data subjected to the beam forming but prior to being subjected to envelope detection processing;
   (c) data subjected to the envelope detection processing but prior to being subjected to logarithmic compression processing; and
   (d) data subjected to the logarithmic compression processing but prior to being subjected to scan conversion.

4. The processing apparatus according to claim 3, wherein
   when the first subject data corresponds to the data prior to being subjected to the beam forming, the beam forming is performed based on the second subject data output by the trained model,
   when the first subject data corresponds to the data subjected to the beam forming and prior to being subjected to the envelope detection processing, the envelope detection processing is performed based on the second subject data output by the trained model,
   when the first data subject corresponds to the data subjected to the envelope detection processing and prior to being subjected to the logarithmic compression processing, the logarithmic compression processing is performed based on the second subject data output by the trained model, and
   when the first subject data corresponds to the data subjected to the logarithmic compression processing and prior to being subjected to the scan conversion, the scan conversion is performed based on the second subject data output by the trained model.

5. The processing apparatus according to claim 1, wherein the trained model is a convolution neural network.

6. An ultrasound apparatus comprising:
   ultrasound transmission and reception circuitry configured to obtain first subject data including a fundamental wave signal and a harmonic signal using a probe through transmission of an ultrasound wave into a subject; and
   processing circuitry configured to:
      acquire the first subject data from the ultrasound transmission and reception circuitry; and
      input the acquired first subject data into a trained model; and
      acquire second subject data output from the trained model, the second subject data corresponding to data in which an amplitude of the fundamental wave signal of the ultrasound wave included in the first subject data is reduced and which is based on an amplitude of a harmonic signal of the ultrasound wave included in the first subject data which is increased,
   wherein the trained model is a model that has been trained, based on input of first ultrasound wave data to output second ultrasound wave data corresponding to data in which an amplitude of a fundamental wave signal included in the first ultrasound wave data is reduced, and which is based on an amplitude of a harmonic signal included in the first ultrasound wave data which is increased.

7. A processing apparatus comprising processing circuitry configured to:
   acquire first subject data including a fundamental wave signal and a harmonic signal of an ultrasound wave;
   input the acquired first subject data into a trained model; and acquire second subject data output from the trained model, the second subject data corresponding to data in which an amplitude of the fundamental wave signal of the ultrasound wave included in the first subject data is reduced, and which is based on an amplitude of the harmonic signal of the ultrasound wave included in the first subject data which is increased, wherein the trained model is a model that has been trained, based on input of first ultrasonic image data, to output second ultrasonic image data corresponding to data in which an amplitude of a fundamental wave signal included in the first ultrasonic image data is reduced, and which is based on an amplitude of a harmonic signal included in the first ultrasonic image data which is increased.

* * * * *